United States Patent [19]

Acher et al.

[11] Patent Number: 5,110,824
[45] Date of Patent: May 5, 1992

[54] METHOD OF TREATING DISORDERS OF COGNITIVE FUNCTION WITH SUBSTITUTED BENZAMIDES

[75] Inventors: Jacques Acher, Itteville; Jean-Claude Monier, Lardy; Jean-Paul Schmitt, Arpajon; Renee Gardaix-Luthereau, Cachan, all of France; Brenda Costall; Robert Naylor, both of Ilkey, United Kingdom

[73] Assignee: Societe D'Etudes Scientifiques et Industrielles de L'Ile-de-France, Paris, France

[21] Appl. No.: 507,753

[22] Filed: Apr. 12, 1990

[30] Foreign Application Priority Data

Apr. 12, 1989 [FR] France ................... 89 04792

[51] Int. Cl.$^5$ .................. A01N 43/76; A01N 43/50
[52] U.S. Cl. .................. 514/377; 514/401; 514/402
[58] Field of Search ............ 514/237.8, 392, 377, 514/401, 402

[56] References Cited

U.S. PATENT DOCUMENTS 4,835,172  5/1989  Acher et al. ............ 514/392
4,906,626  3/1990  Amrein et al. ........... 514/237.8

Primary Examiner—Frederick E. Waddell
Assistant Examiner—T. J. Criares
Attorney, Agent, or Firm—Fitzpatrick, Cella, Harper & Scinto

[57] ABSTRACT

The invention relates to the use of benzamide derivatives of the formula:

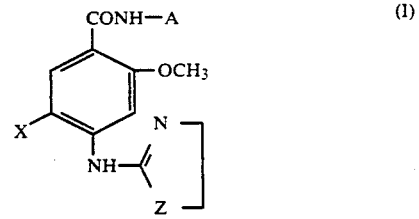

in which:
A is a diethylaminoethyl group or a group of the formula II:

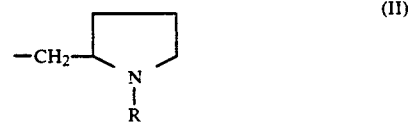

where R is a $C_1$-$C_3$ alkyl, allyl, cyclopropylmethyl or cyclohexenylmethyl group,
X is a chlorine or bromine atom, and
Z is —NH— or —O— with the following condition: when Z is —O—, A is a diethylaminoethyl group, and their pharmacologically acceptable salts for the preparation of medicinal products which are useful in the treatment and prevention of disorders of the cognitive function.

9 Claims, 16 Drawing Sheets

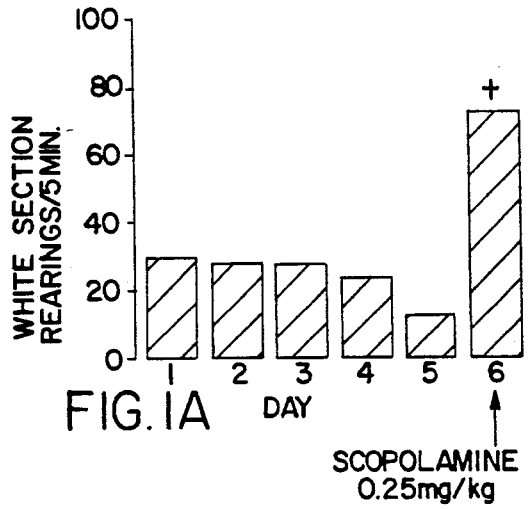
FIG.1A
FIG.1C
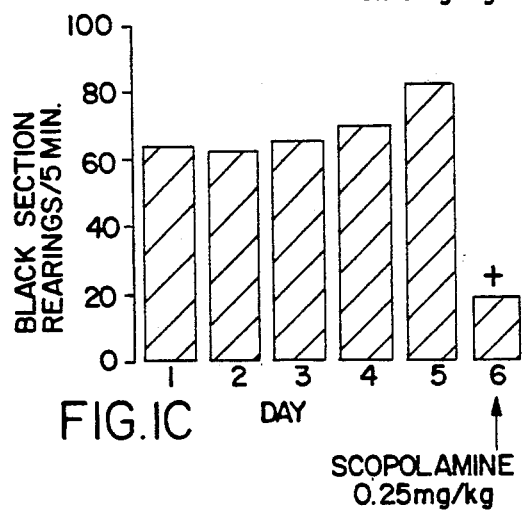
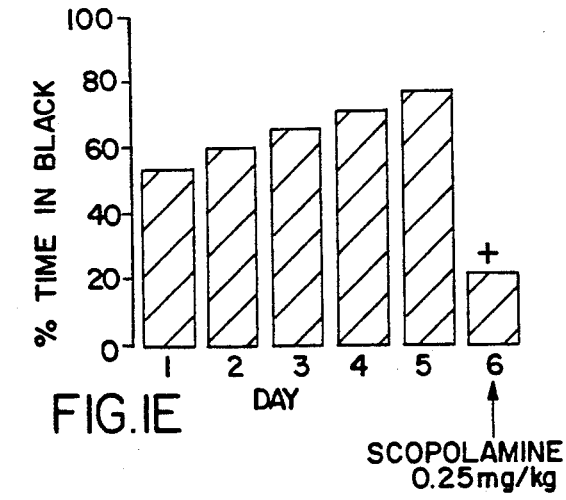
FIG.1E
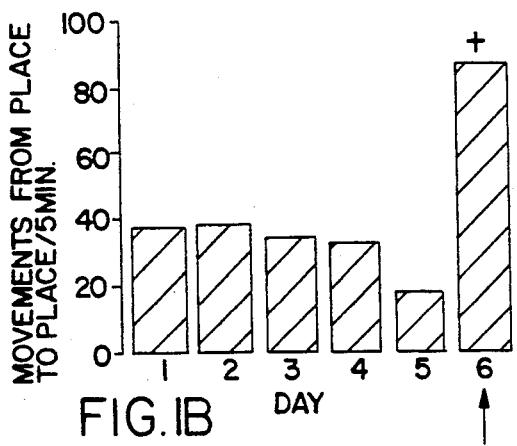
FIG.1B
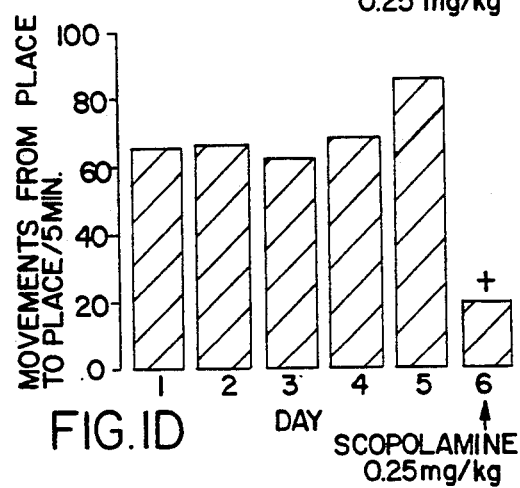
FIG.1D
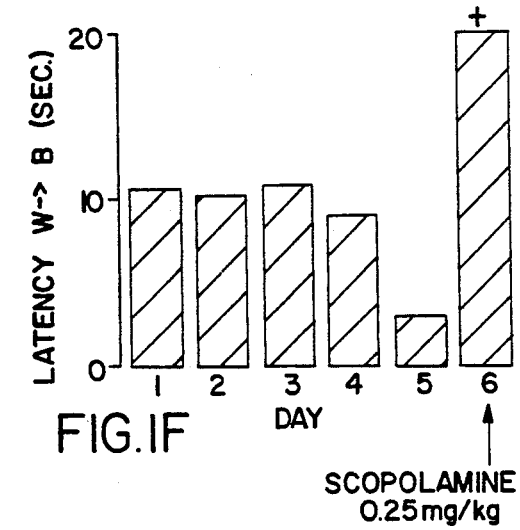
FIG.1F

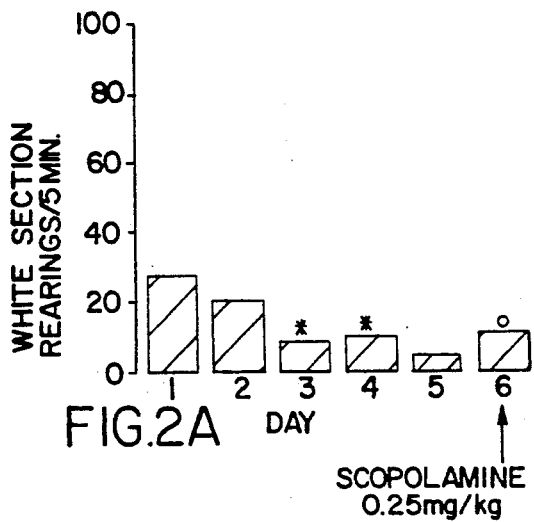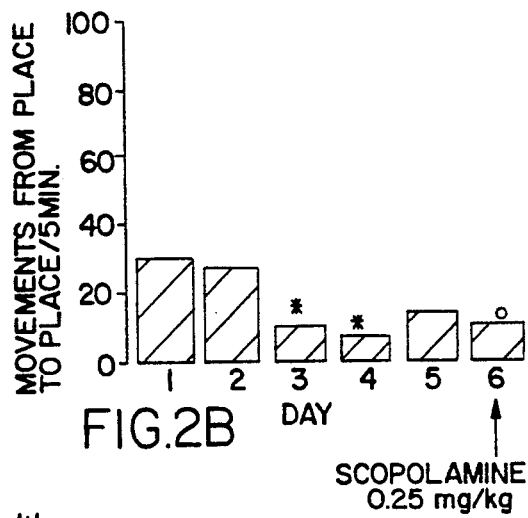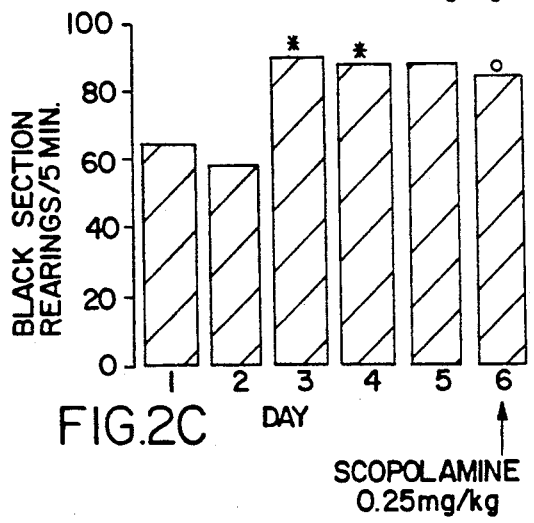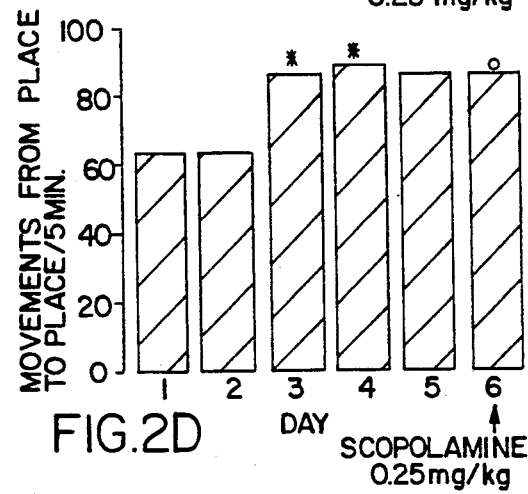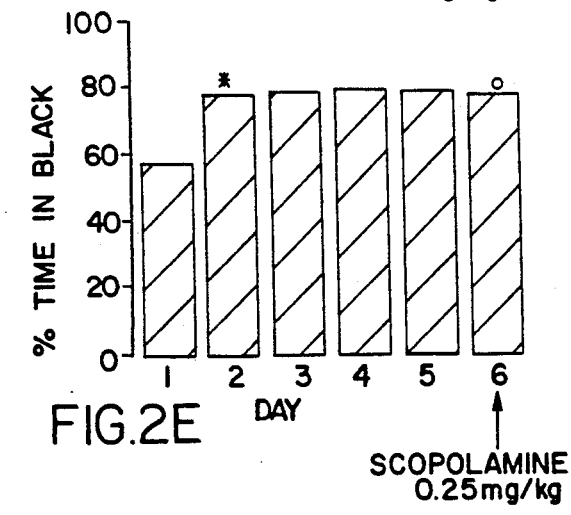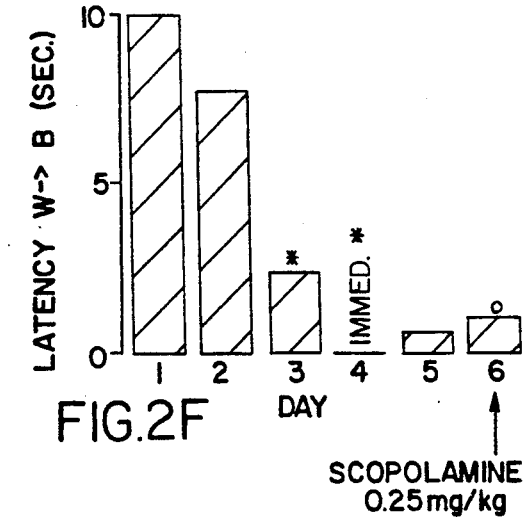

SCOPOLAMINE 0.25 mg/kg

SCOPOLAMINE 0.25mg/kg

SCOPOLAMINE 0.25mg/kg

SCOPOLAMINE 0.25mg/kg

SCOPOLAMINE 0.25mg/kg

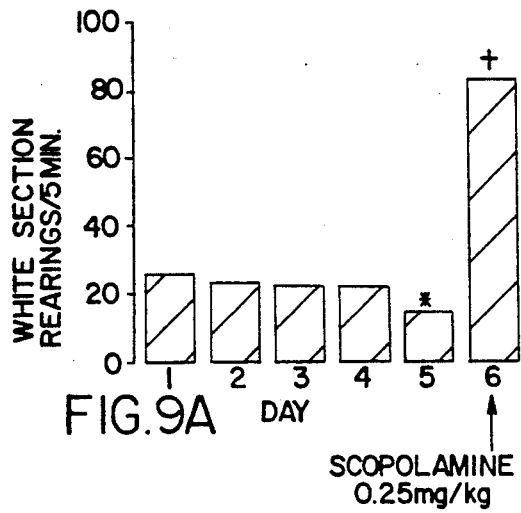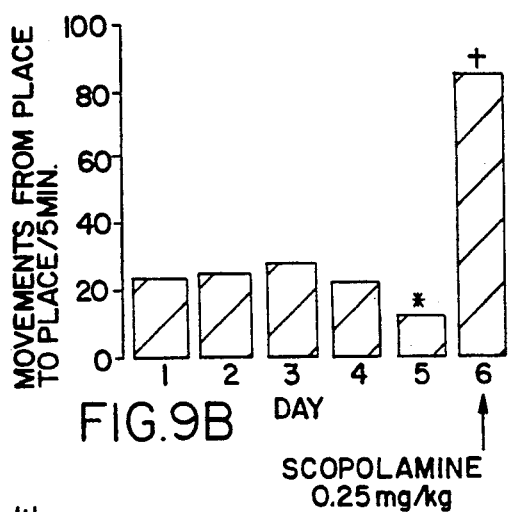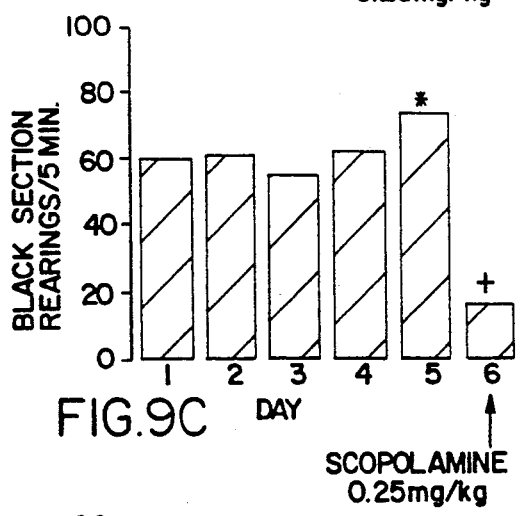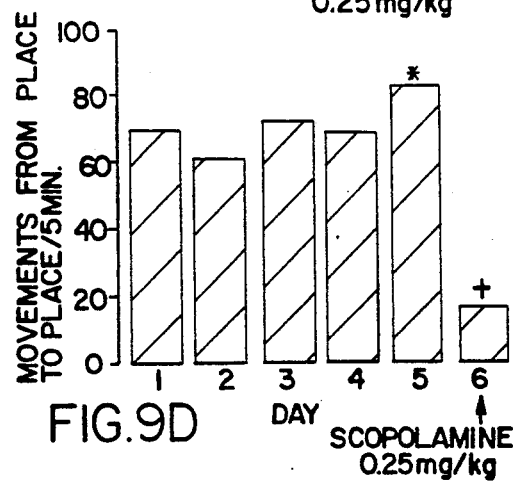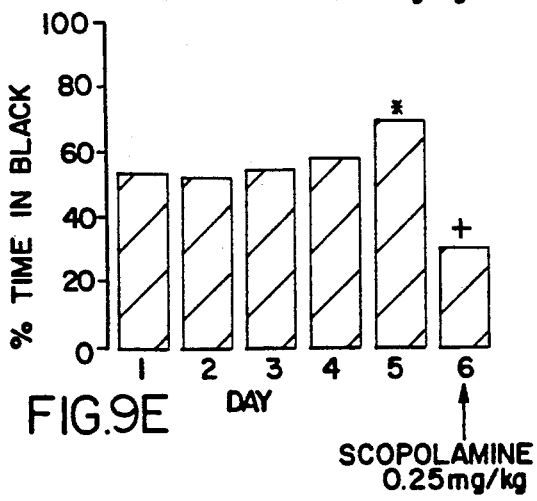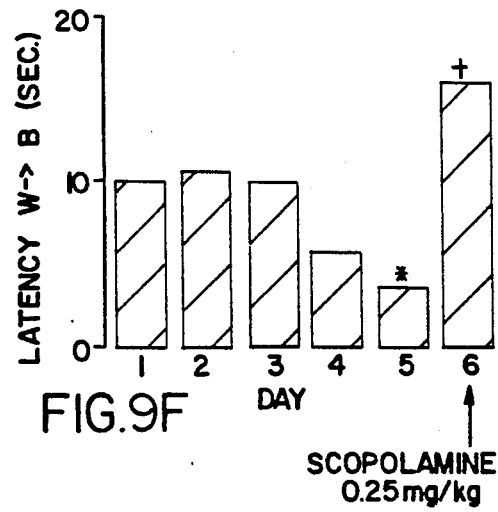

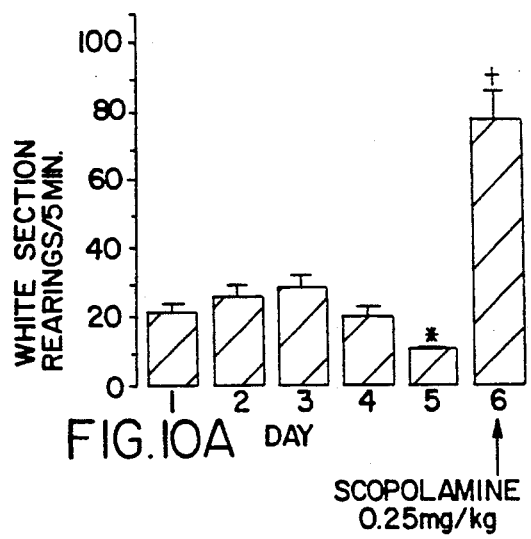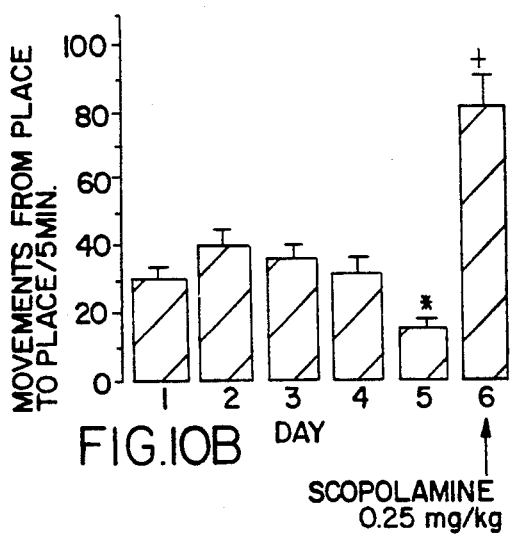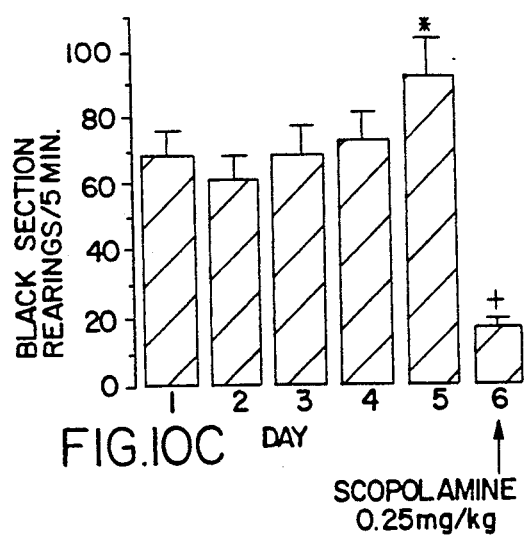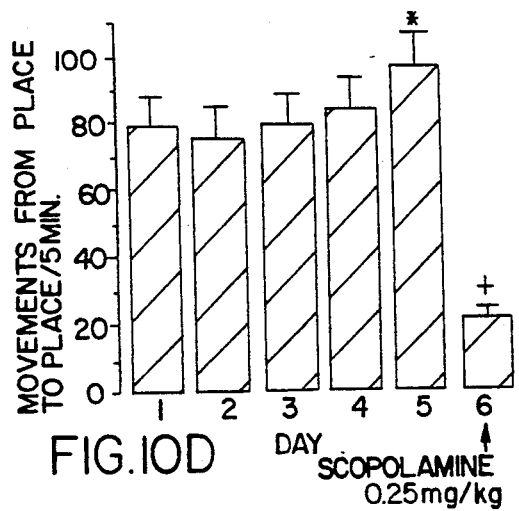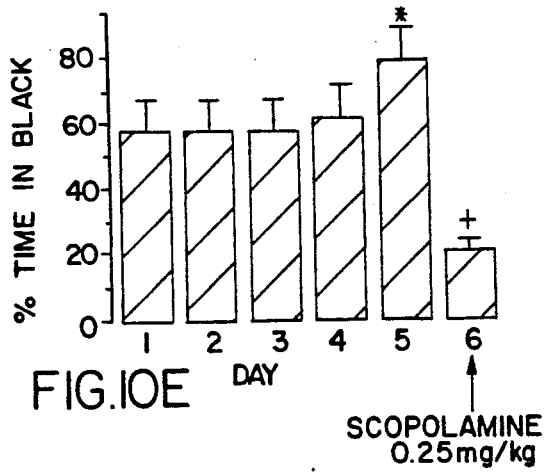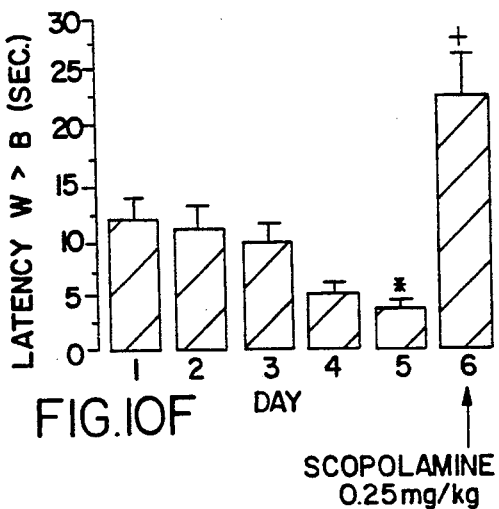

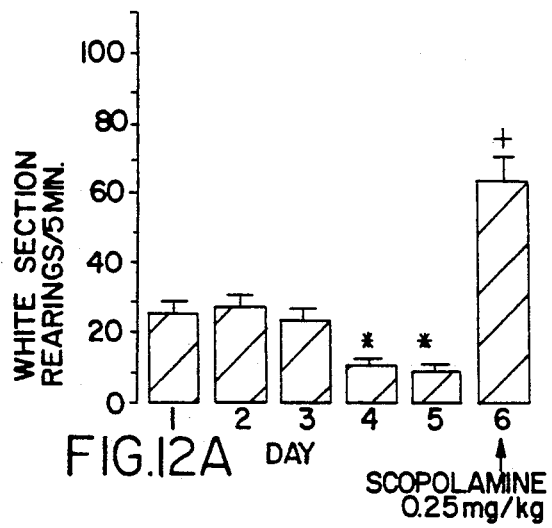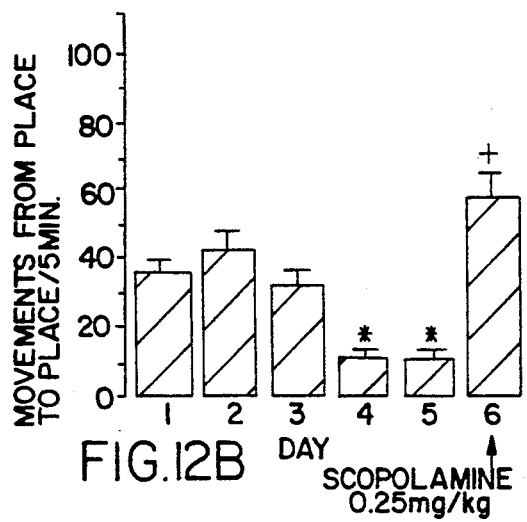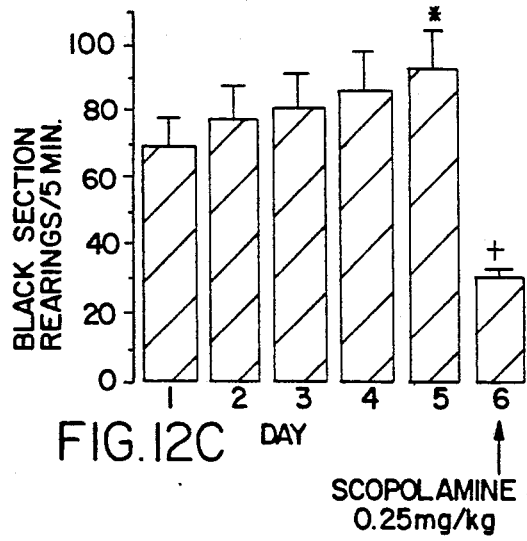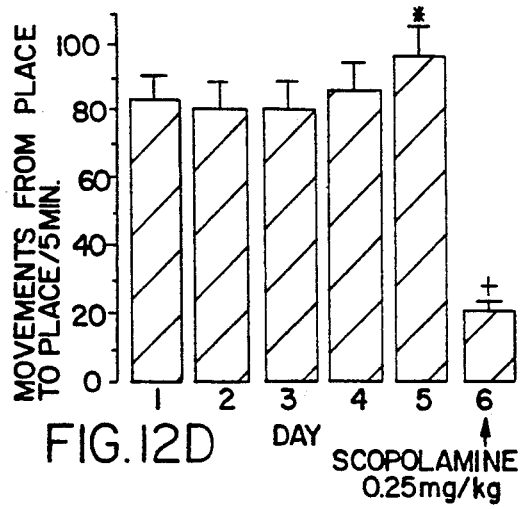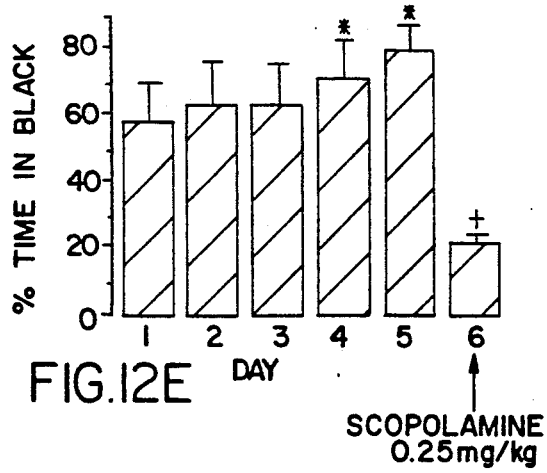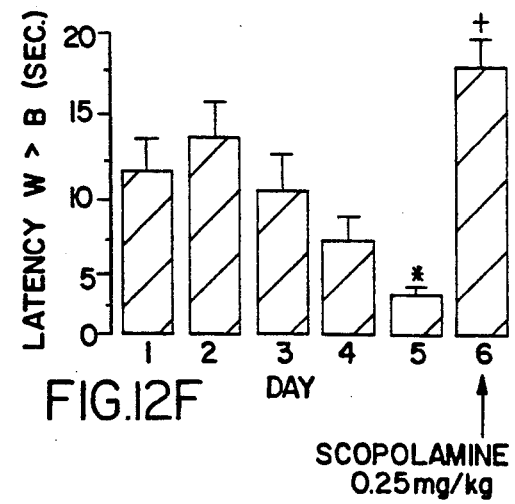

METHOD OF TREATING DISORDERS OF COGNITIVE FUNCTION WITH SUBSTITUTED BENZAMIDES

BACKGROUND OF THE INVENTION

1. Field of the Invention

The compounds of the present invention and the method of their preparation is described in French Patent No. 2,592,042 and U.S. Pat. No. 4,835,172, issued May 30, 1989, the disclosures of which are incorporated herein by reference. Such compounds are described therein as central nervous system activators and as antidepressants.

Some of these compounds have also evinced gastromotor properties which have formed of U.S. application Ser. No. 450,422 (pending) or anxiolytic and antipsychotic properties which have formed the subject of European Patent Application No. 295,350 and U.S. application Ser. No. 454,015 pending.

It has been discovered that the compounds of formula (I), as defined hereafter are endowed with a specific and completely unexpected property: the improvement of cognitive and memory functions.

SUMMARY OF THE INVENTION

Accordingly, the present invention relates to a method of treating and preventing disorders of cognitive function which comprises administering a therapeutically effective amount of a compound of the general formula (I):

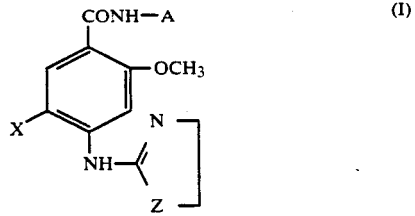

in which:

A is a diethylaminoethyl group or a group of the general formula II

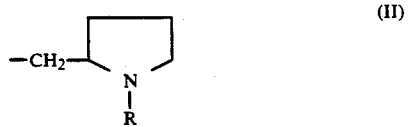

where R is a $C_1$-$C_3$ alkyl, allyl, cyclopropylmethyl or cyclohexenylmethyl group, X is a chlorine or bromine atom, and Z is —NH— or —O— with the following condition: when Z is —O—, A is a diethylaminoethyl group, and their pharmacologically acceptable salts.

DESCRIPTION OF THE PREFERRED EMBODIMENTS

Figure 3A:
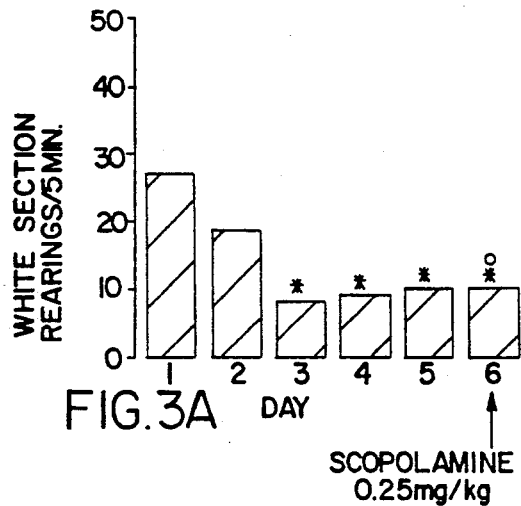
Figure 3B:
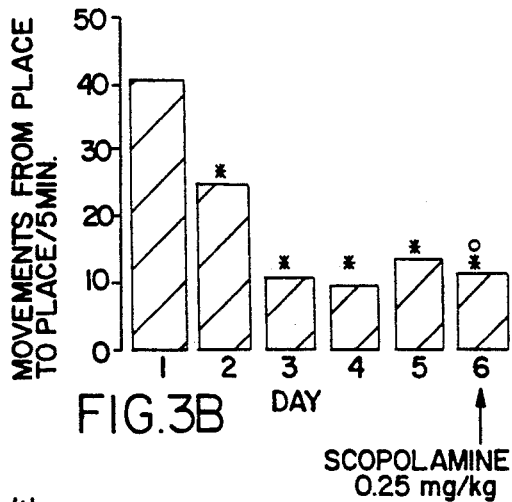
Figure 3C:
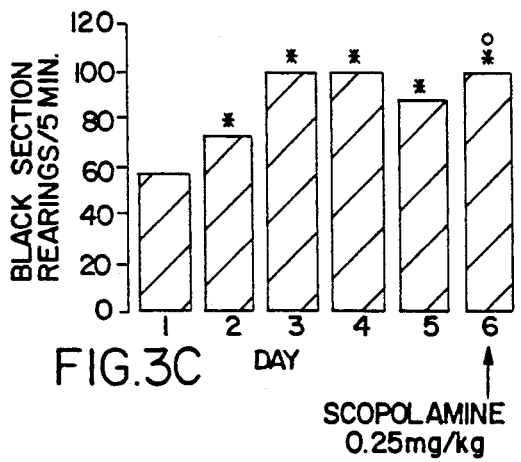
Figure 3D:
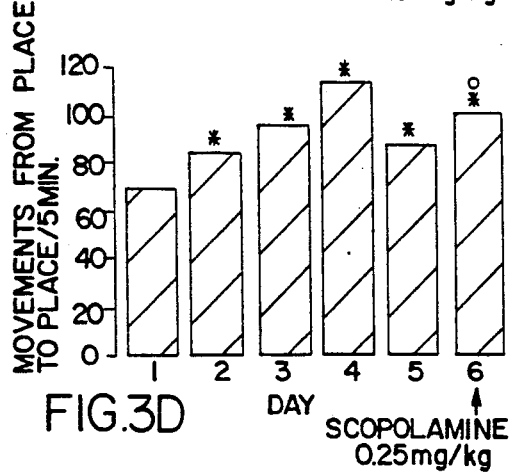
Figure 3E:
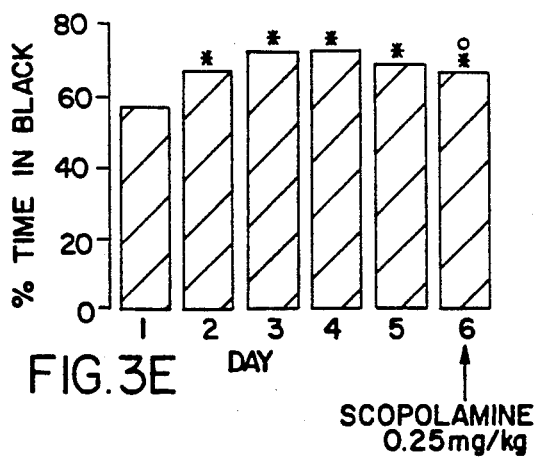
Figure 3F:
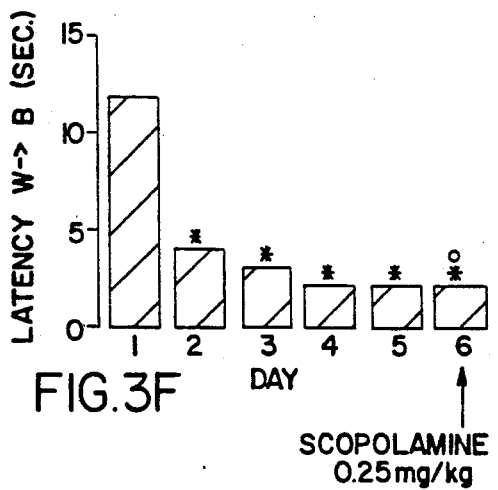
Figure 4A:
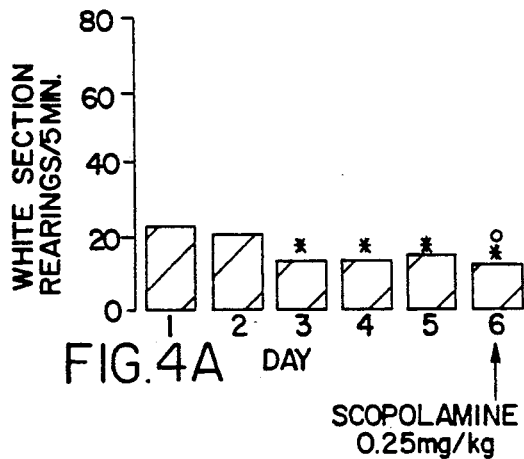
Figure 4B:
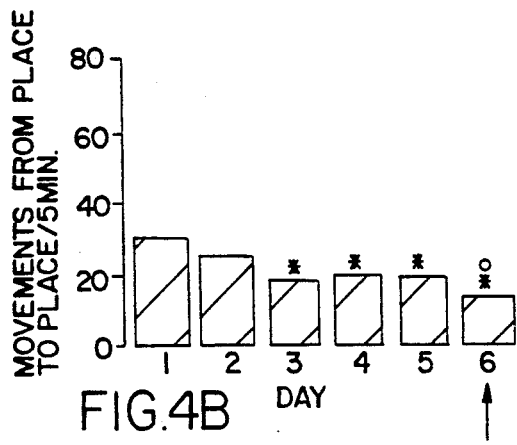
Figure 4C:
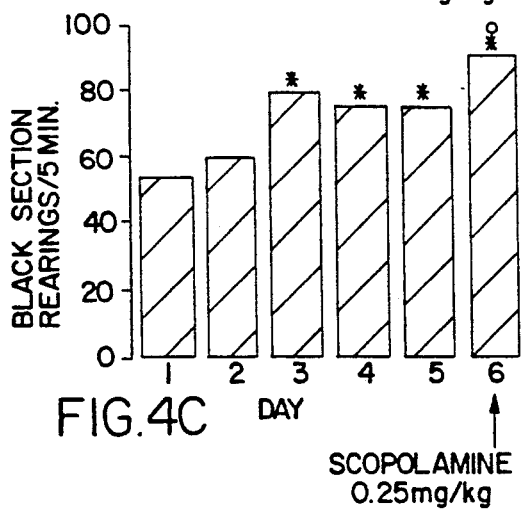
Figure 4D:
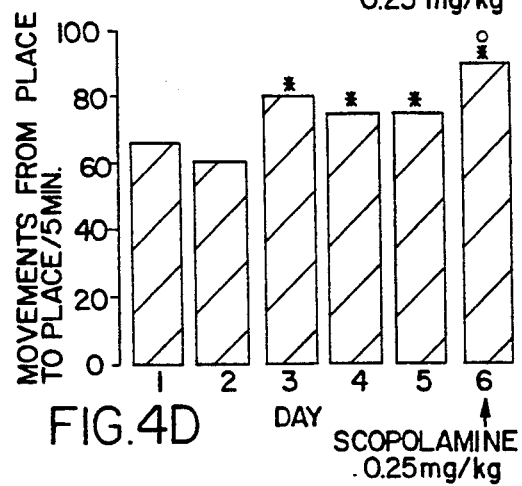
Figure 4E:
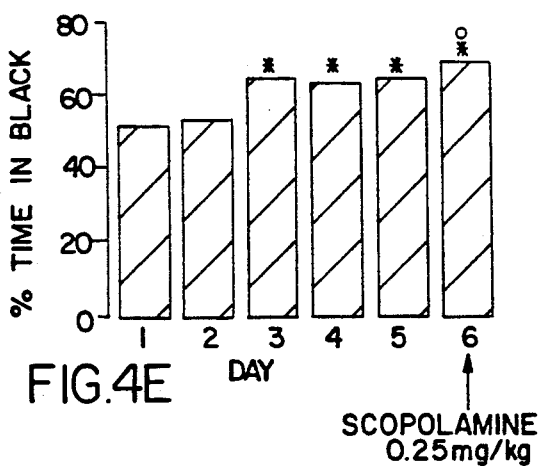
Figure 4F:
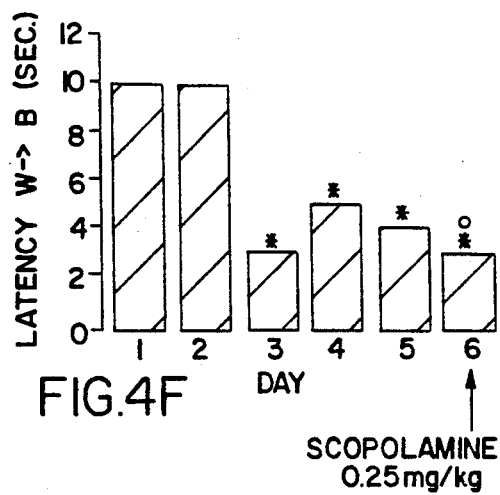
Figure 5A:
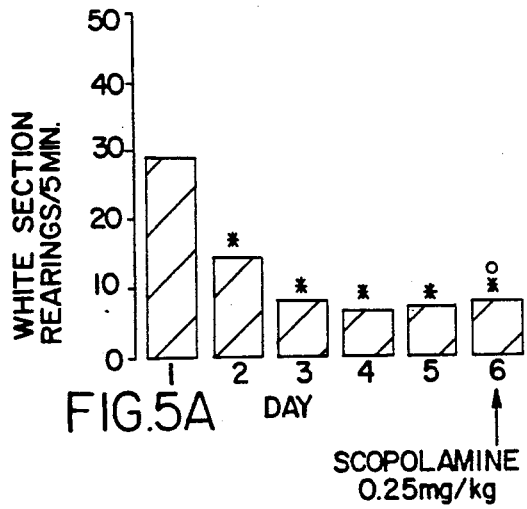
Figure 5B:
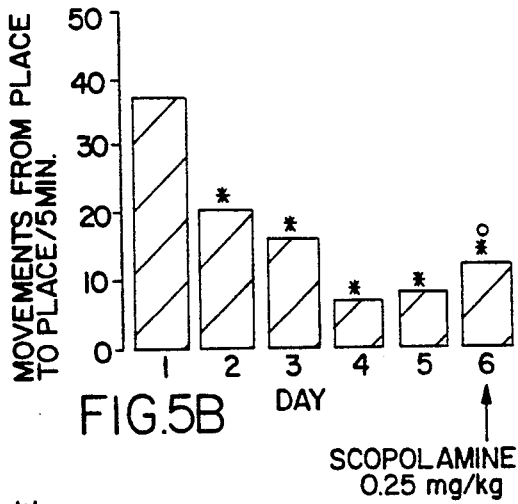
Figure 5C:
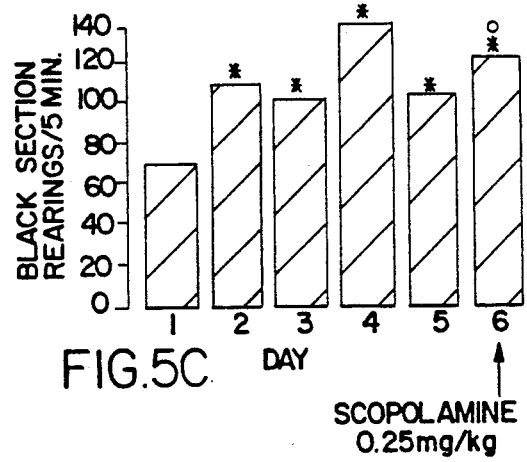
Figure 5D:
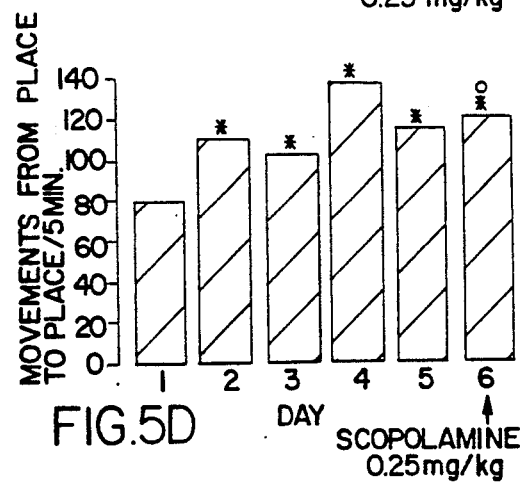
Figure 5E:
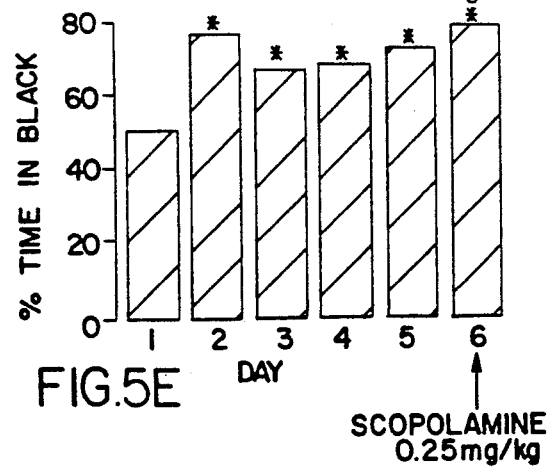
Figure 5F:
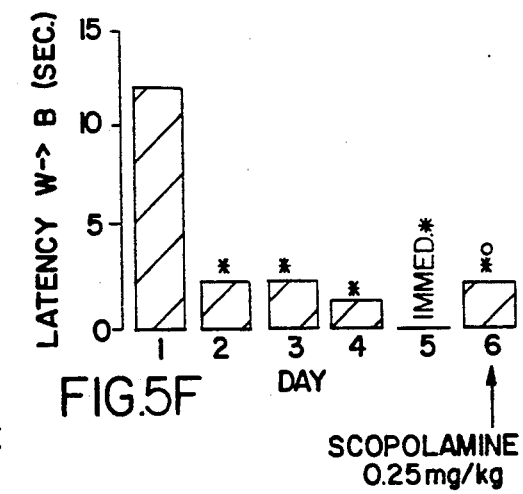
Figure 6A:
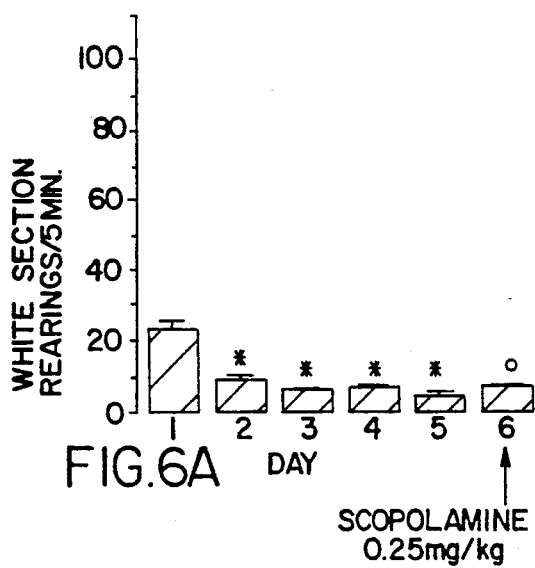
Figure 6B:
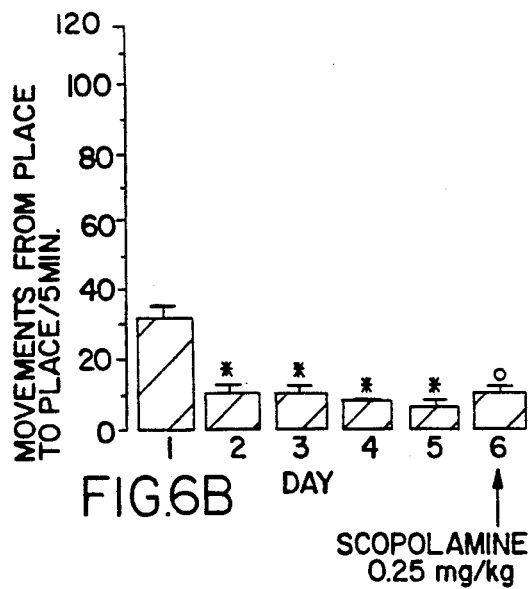
Figure 6C:
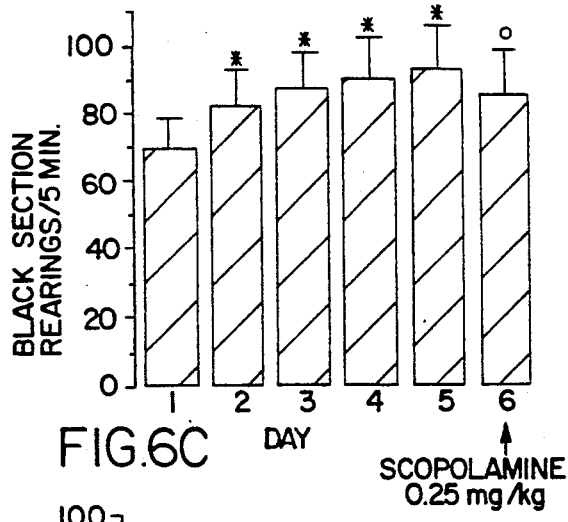
Figure 6D:
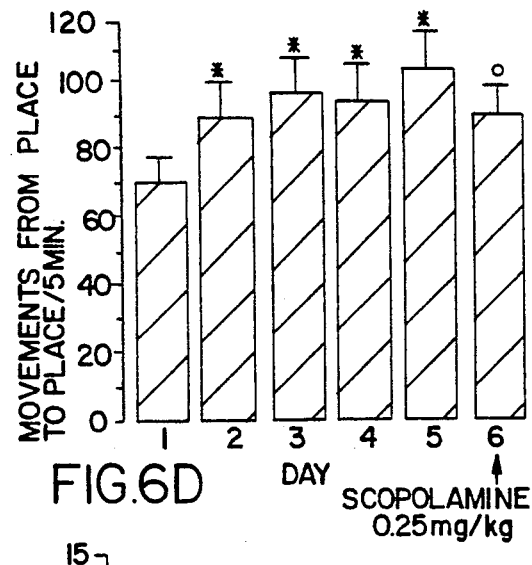
Figure 6E:
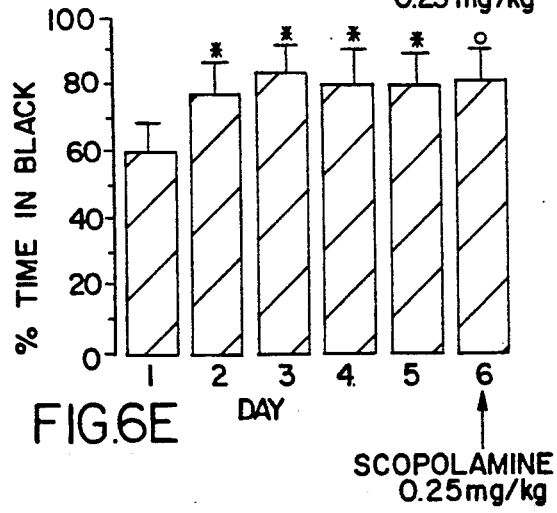
Figure 6F:
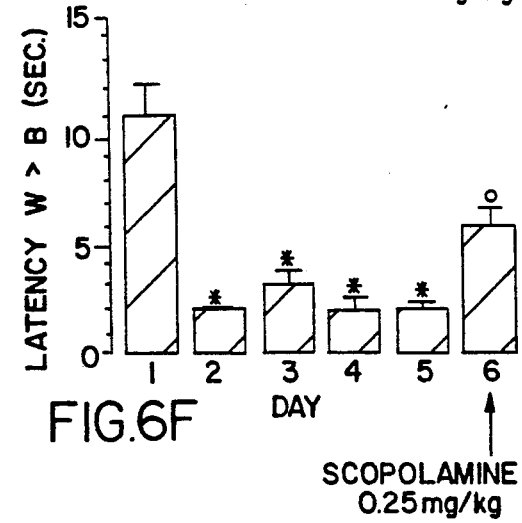
Figure 7A:
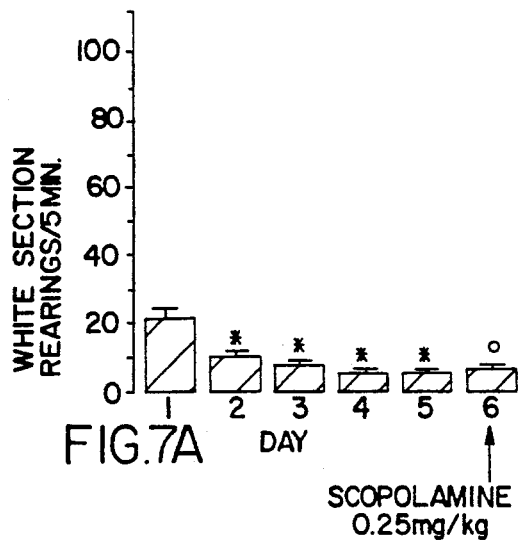
Figure 7B:
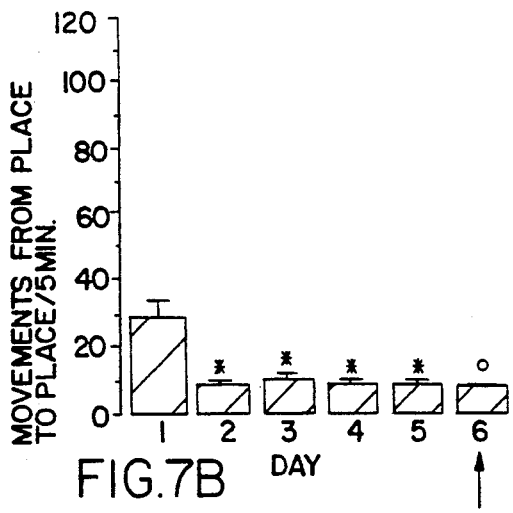
Figure 7C:
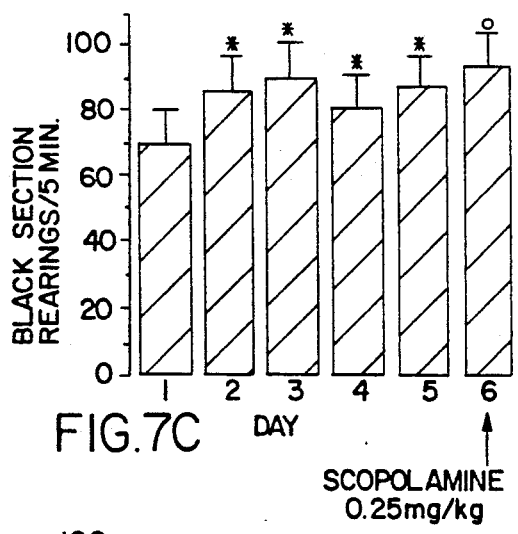
Figure 7D:
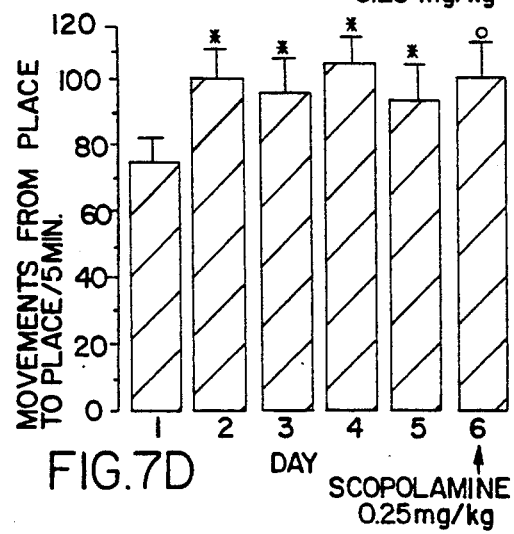
Figure 7E:
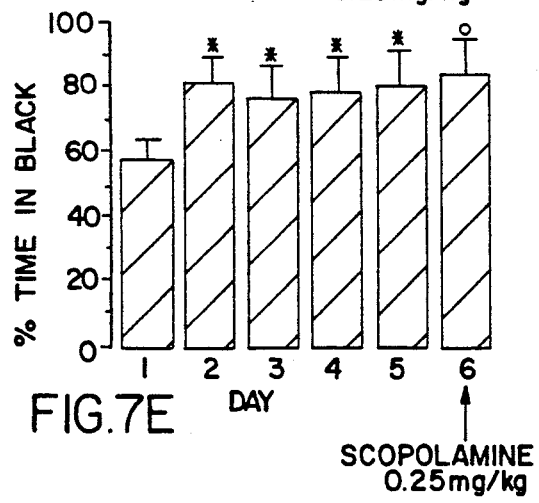
Figure 7F:
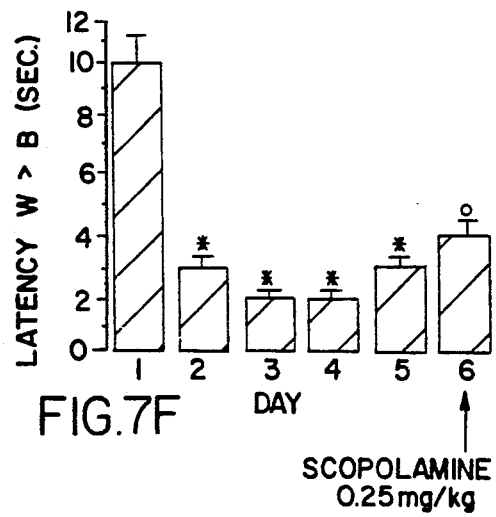
Figure 8A:
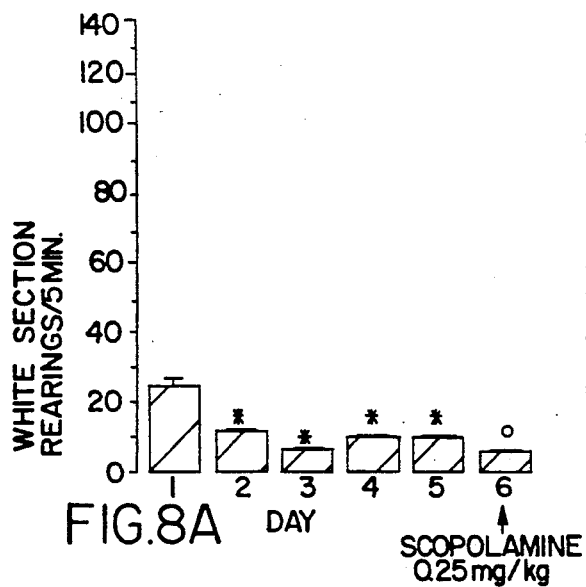
Figure 8B:
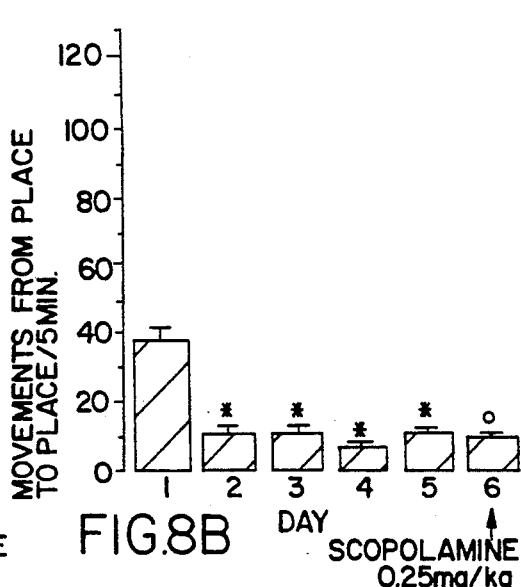
Figure 8C:
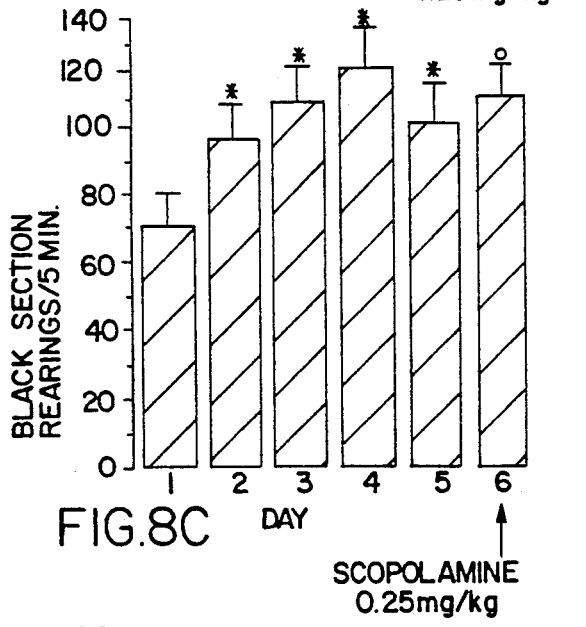
Figure 8D:
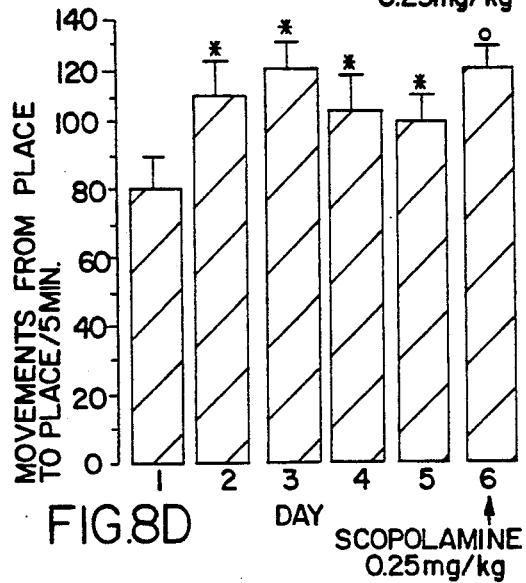
Figure 8E:
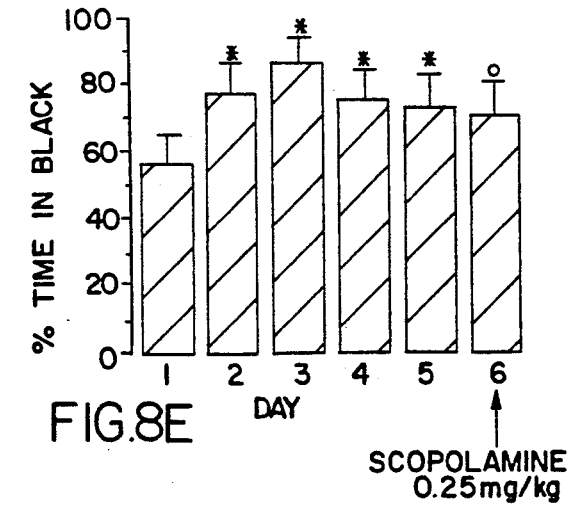
Figure 8F:
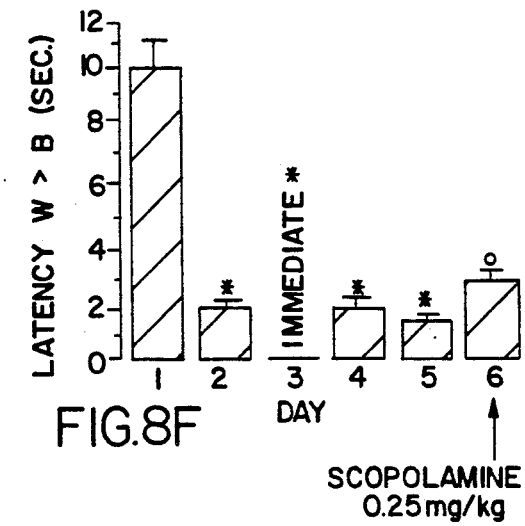
Figure 11A:
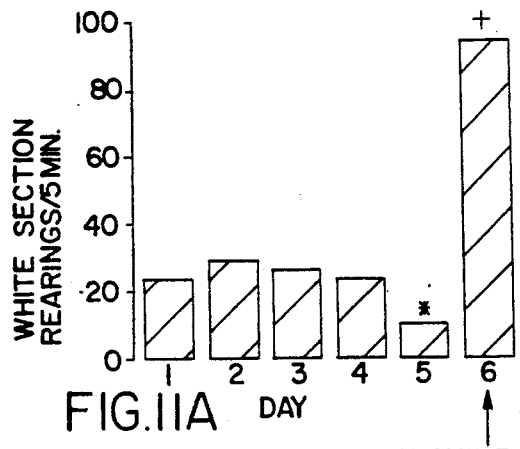
Figure 11B:
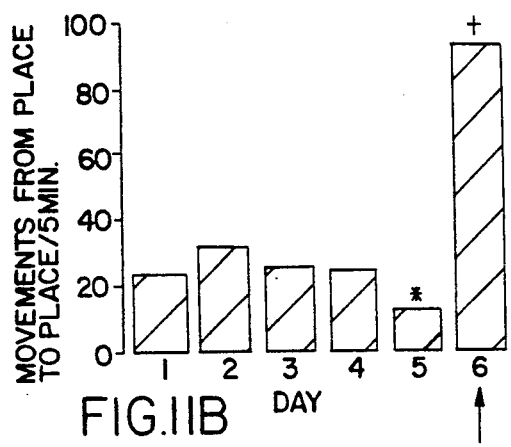
Figure 11C:
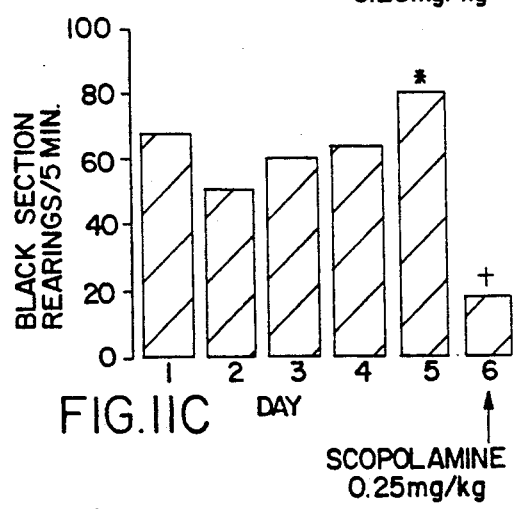
Figure 11D:
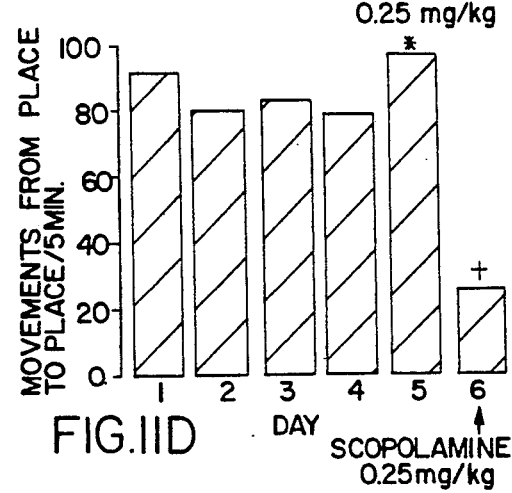
Figure 11E:
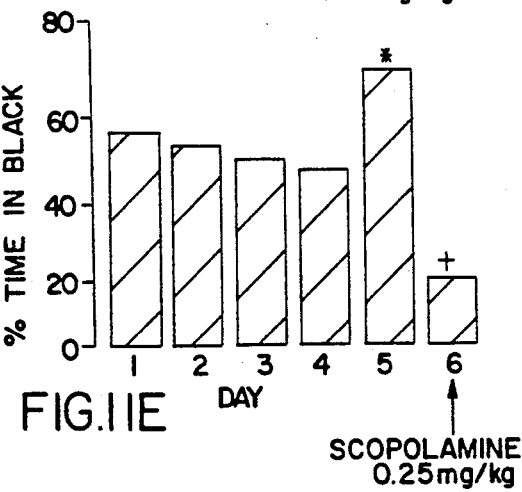
Figure 11F:
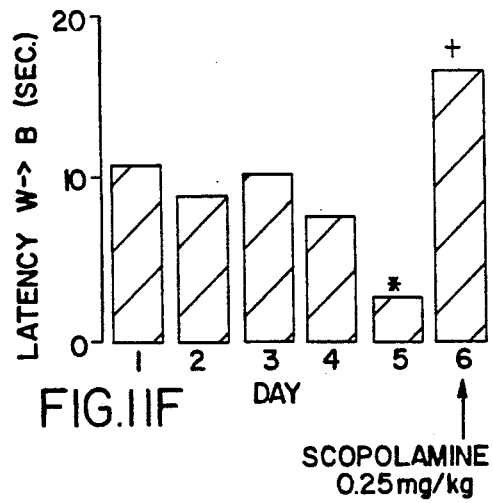
Figure 13A:
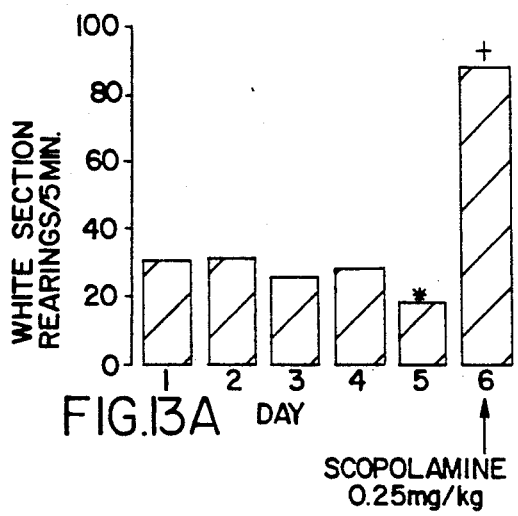
Figure 13B:
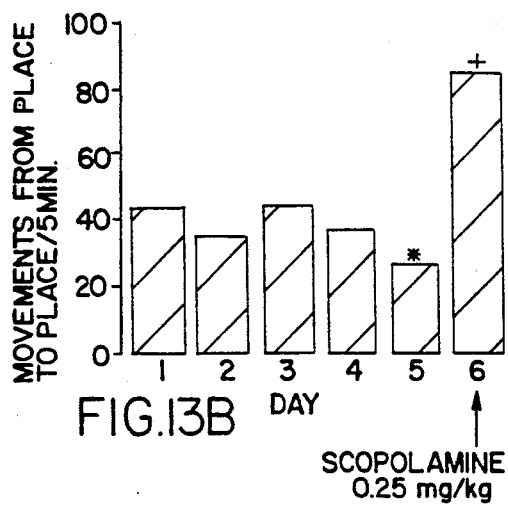
Figure 13C:
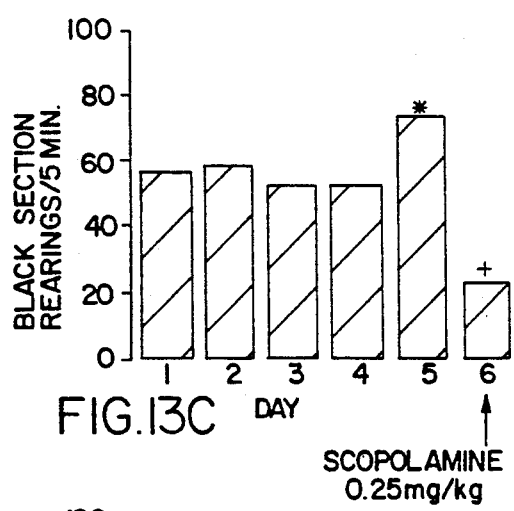
Figure 13D:
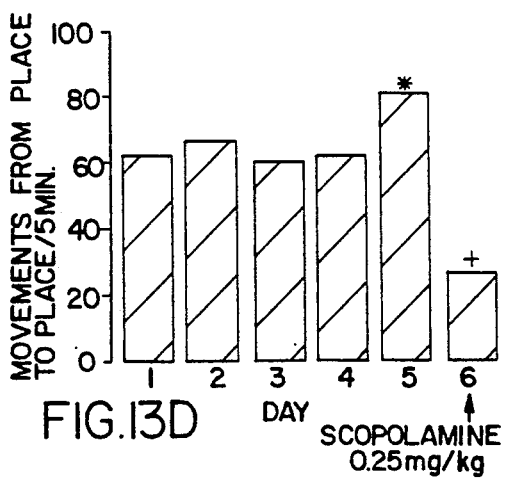
Figure 13E:
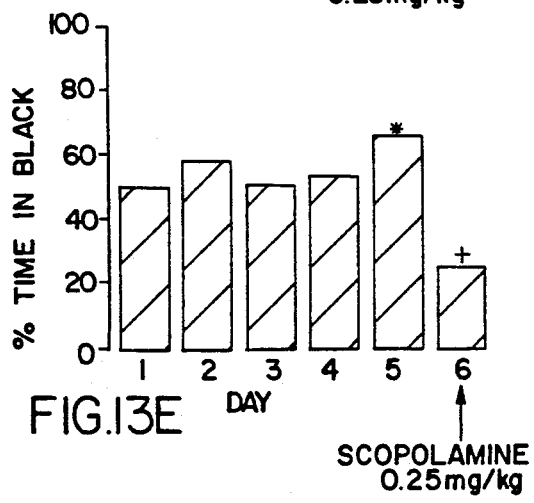
Figure 13F:
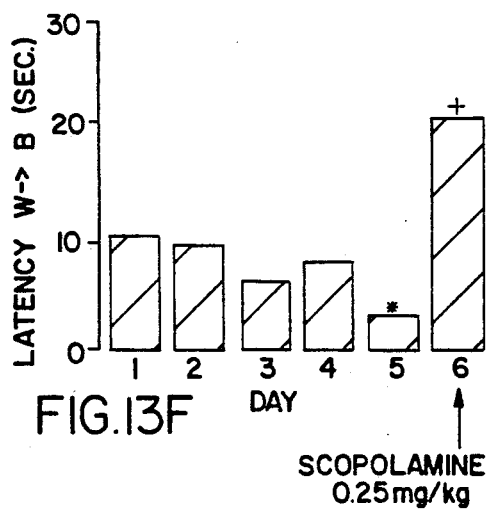

The invention relates especially to the use of the following preferred compounds to treat cognitive disorders:

Compound 1: N-[2-(diethylamino)ethyl]-2-methoxy-4-[(4,5-dihydro-1H-imidazol-2-yl)amino]-5-chlorobenzamide;

Compound 2: N-(1-allyl-2-pyrrolidinylmethyl)-2-methoxy-4-[(4,5-dihydro-1H-imidazol-2-yl)amino]-5-chlorobenzamide;

Compound 3: N-(1-methyl-2-pyrrolidinylmethyl)-2-methoxy-4-[(4,5-dihydro-1H-imidazol-2-yl)amino]-5-chlorobenzamide;

Compound 4: N-[2-(diethylamino)ethyl]-2-methoxy-4-[(4,5-dihydro-2-oxazolyl)amino]-5-chlorobenzamide;

Compound 5: N-(1-cyclopropylmethyl-2-pyrrolidinylmethyl)-2-methoxy-4-[(4,5-dihydro-1H-imidazol-2-yl)-amino]-5-chlorobenzamide;

Compound 6: N-(1-cyclohexenylmethyl-2-pyrrolidinylmethyl)-2-methoxy-4-[(4,5-dihydro-1H-imidazol-2-yl)-amino]-5-chlorobenzamide;

Compound 7: N-[2-(diethylamino) ethyl]-2-methoxy-4-[(4,5-dihydro-1H-imidazol-2-yl)amino]5-bromobenzamide; and Compound 8: N-(1-propyl-2-pyrrolidinylmethyl)-2-methoxy-4-[(4,5-dihydro-1H-imidazol-2-yl)amino]-5-chlorobenzamide.

The improvement of cognitive and memory functions by the use of the present compounds was demonstrated in pharmacological tests performed on rodents and primates, in particular in a habituation test in mice and in a learning test in marmoset monkeys. The tests were conducted as follows:

I - HABITUATION TEST IN YOUNG ADULT MICE

In a box divided by a pierced partition into 2 compartments, one white and brightly lit, the other black and dimly lit, mice naturally habituated to a dark environment were placed in the middle of the white compartment. To flee this assault, they took refuge in the dark compartment. At the beginning, they explored the white compartment, and they took 8 to 15 seconds to locate the opening between the 2 compartments. The experiment was repeated for several days, and they "learned" to flee without prior exploration of the white compartment. After about 5 to 6 days, flight was immediate and they explored the dark compartment at greater length.

The habituation is thus characterized by a decrease in the time required to pass from the white compartment to the dark compartment and by an increase in the exploration of the dark compartment (increase in the number of rearings and of movements from place to place) in preference to the white compartment.

This habituation process was impaired by the administration of scopolamine.

TEST PROCEDURE:

The following parameters were measured under video monitoring on albino male mice weighing 25-30 g, every day for 5 minutes:

(1) the latency time before passing from the white compartment to the dark compartment;

(2) the number of exploratory rearings in each of the compartments during the test;

(3) the number of lines crossed on the square-ruled floor of the 2 compartments, reflecting exploratory locomotion; and (4) the percentage of time spent in the dark compartment.

These measurements were made on groups of mice receiving either an inert vehicle or a compound according to the invention administered subcutaneously twice daily at a subanxiolytic dose (1 ng/kg for the Compound 1, 10 ng/kg for the Compounds 2-4, 1 μg/kg for the Compounds 5 and 6 and 10 μg/kg for the Compound 7). The effect of the acute administration of scopolamine, injected intraperitoneally at a dose of 0.25 mg/kg, was studied in the control group and in the treated groups after acquisition of the habituation.

The effect of Compound 1 of the invention (1 ng/kg administered subcutaneously twice daily) on the impairment of the habituation produced by chronic administration of scopolamine (0.25 mg/kg per day) was also studied.

The same measurements were carried out with compounds of similar formula to that of the compounds of the present invention. These compounds, also described in the French Patent No. 2,592,042, were used in the present case as reference compounds.

The reference compounds were the following:

Reference Compound A: N-(1-ethyl-2-pyrrolidinylmethyl)-2-methoxy-3,5-dibromo-4-[(4,5-dihydro-1H-imidazol-2-yl)amino]benzamide;

Reference Compound B: N-[2-(diethylamino)ethyl]-[-2-methoxy-4-[4,5-dihydro-4-methyl-1H-imidazol-2-yl)amino]-5-chlorobenzamide; and Reference Compound C: N-[2-(diethylamino)ethyl]-2-methoxy-3,5-dichloro-4-[4,5-dihydro-1H-imidazol-2-yl)amino]benzamide.

These three compounds were administered subcutaneously twice daily at a dose of 10 ng/kg. The same measurements were made with Reference Compounds A and B at a dose of 1 μm/kg.

RESULTS OF THE TEST

The results of the habituation study and of the effect of acute administration of scopolamine are shown in Tables 1 to 13 and is illustrated in FIGS. 1A to 13F.

FIGS. 1A to 1F represents the results of the measurements of the parameters used as indicators of the habituation process in a control group of mice receiving an inert vehicle during five consecutive days, as well as the effect on these parameters of the administration of scopolamine injected intraperitoneally at a dose of 0.25 mg/kg, on the sixth day.

FIGS. 2A-8F represents the results of the measurements of the same parameters as in FIGS. 1A to 1F in groups of mice receiving twice daily a compound according to the invention, administered subcutaneously at a dose of 1 ng/kg for compound 1 (FIGS. 2A-2F), 10 ng/kg for compounds 2, 3 and 4 (FIGS. 3A-3F, 4A-4F and 5A-5F respectively), 1 μg/kg for compounds 5 and 6 (FIGS. 6A-6F and 7A-7F respectively) and 10 μg/kg for compound 7 (FIGS. 8A-8F), during five consecutive days, as well as the effect on these parameters of the administration of scopolamine injected intraperitoneally at a dose of 0.25 mg/kg, on the sixth day.

FIGS. 4A-13F represent the results of the measurements of the same parameters as in FIGS. 1A-1F in groups of mice receiving twice daily a reference compound, administered subcutaneously at a dose of 10 ng/kg and 1 μg/kg for compound A (FIGS. 9A-9F and 10A-10F respectively), 10 ng/kg and 1 μg/kg for compound B (FIGS. 11A-11F and 12A-12F respectively) and 10 ng/kg for compound C (FIGS. 13A-13F), during five consecutive days, as well as the effect on these parameters of the administration of scopolamine injected intraperitoneally at a dose of 0.25 mg/kg on the sixth day.

In the control group, it was found that the mean latency time of 11 seconds at the beginning gradually decreased to a mean minimum of 3.4 seconds, reached after 5 days.

In parallel, the time spent in the black compartment gradually increased and reached approximately 78% after 5 days. The number of movements from place to place and rearings in this compartment also increased, while the time spent and the number of movements from place to place and rearings in the white compartment, decreased. These results collectively demonstrated the habituation process, which stabilized in 5 days.

Administration of scopolamine at a dose of 0.25 mg/kg inhibits the habituation phenomenon. That inhibition is demonstrated by an increased latency time, becoming even longer than the initial latency time, by a decrease in the time spent in the black compartment and also by a decrease in the number of movements from place to place and rearings in that compartment.

In the groups of mice treated with a compound of the invention, it was found that the latency time decreased more quickly, and that its minimum value was, in general, lower and was obtained more rapidly than in the control group.

It was also found that the time spent in the black compartment, as well as the number of movements from place to place and rearings in that compartment, increased significantly from the second or third day onwards, compared with the first day and compared with the control group.

Finally, the administration of scopolamine brought about little or no modification in the group of parameters studied.

In the groups treated with the reference compounds, the habituation process proved similar to that of the control group and the administration of scopolamine produced the same effects.

It is, hence, apparent that the compounds of the invention improve the habituation process and avert the scopolamine-induced disturbances, in contrast to the reference compounds of very similar structure.

Figure 14A:
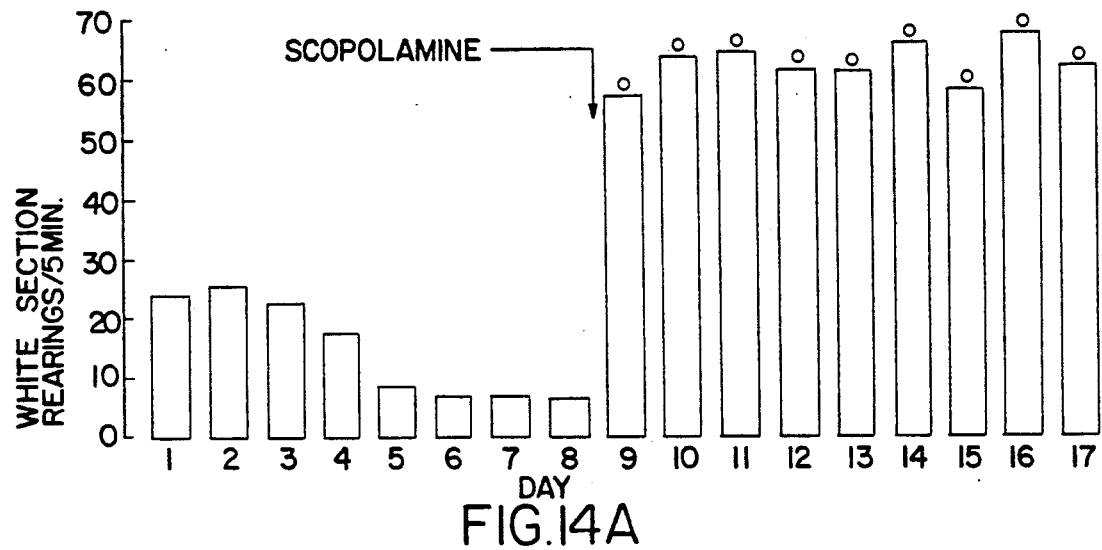

The results of the study of the effects of Compound 1 on the impairment of habituation due to a chronic administration of scopolamine are illustrated in FIG. 14.

Figure 14B:
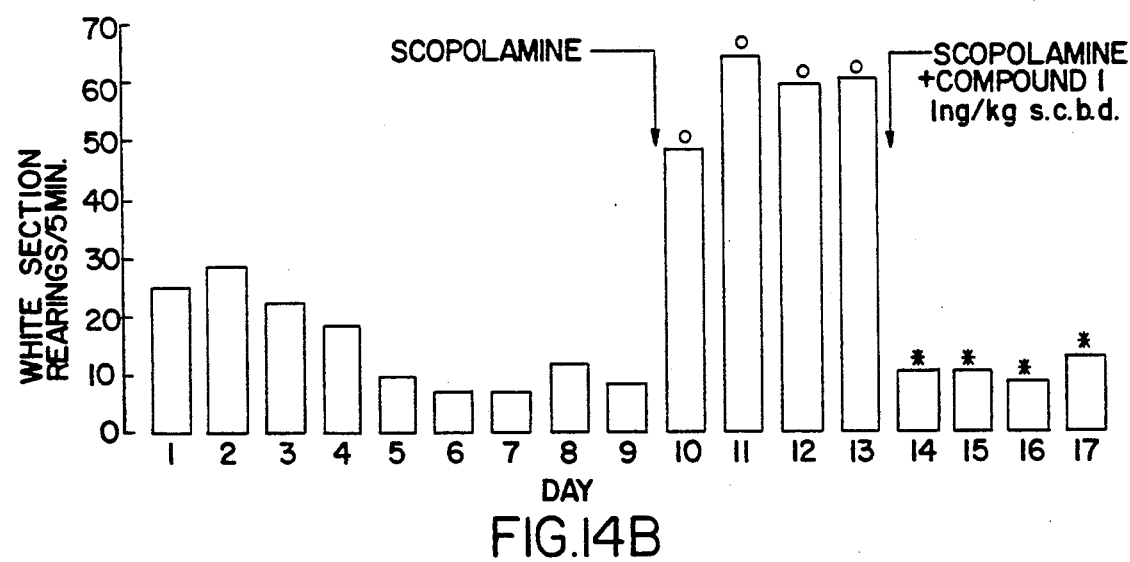
Figure 15A:
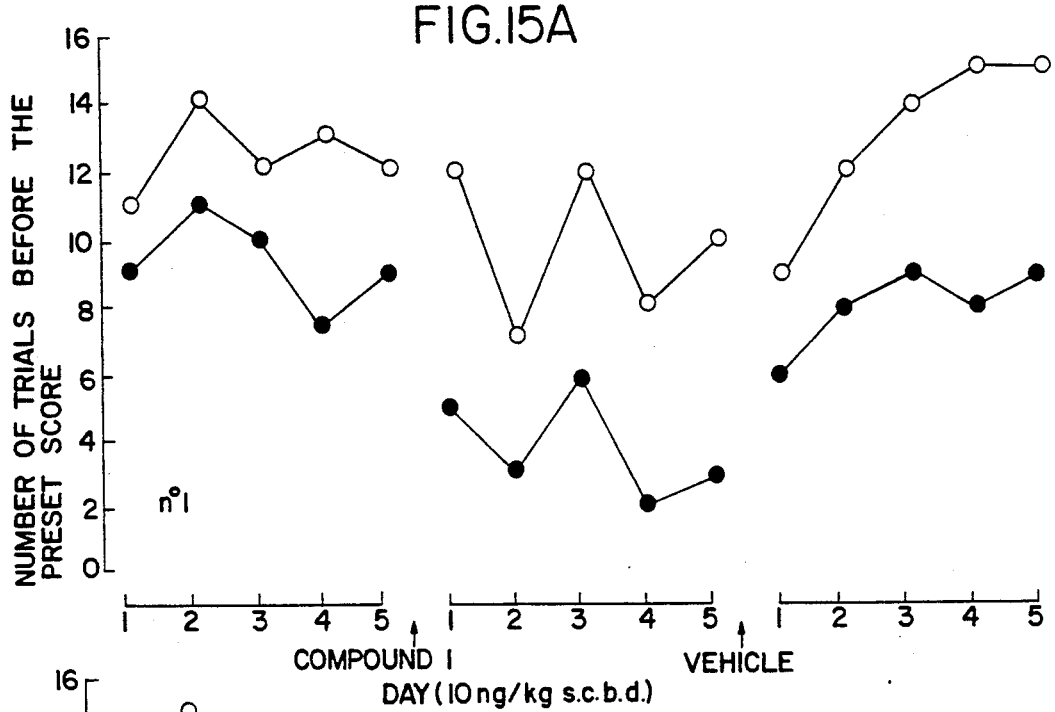
Figure 15B:
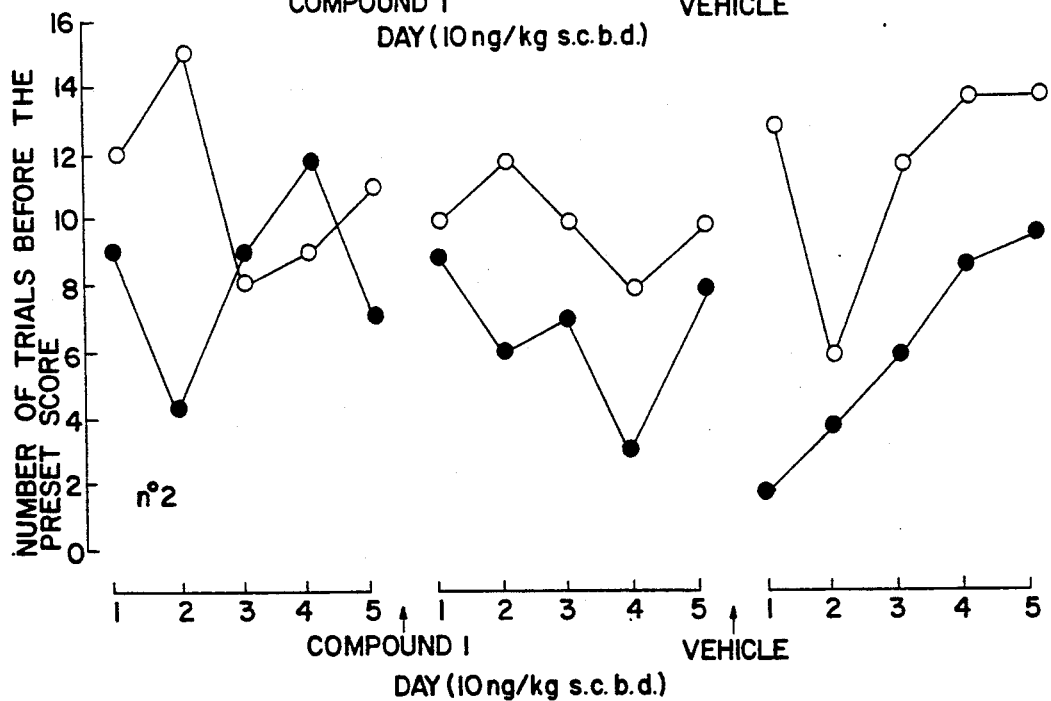
Figure 16A:
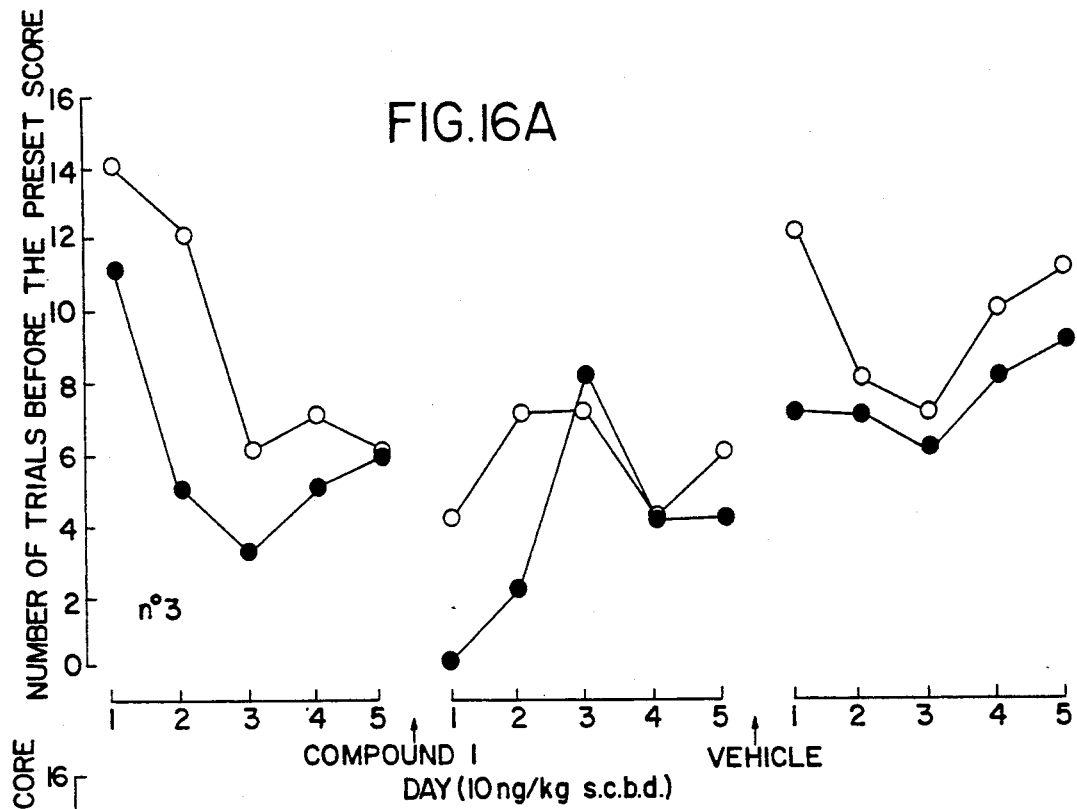
Figure 16B:
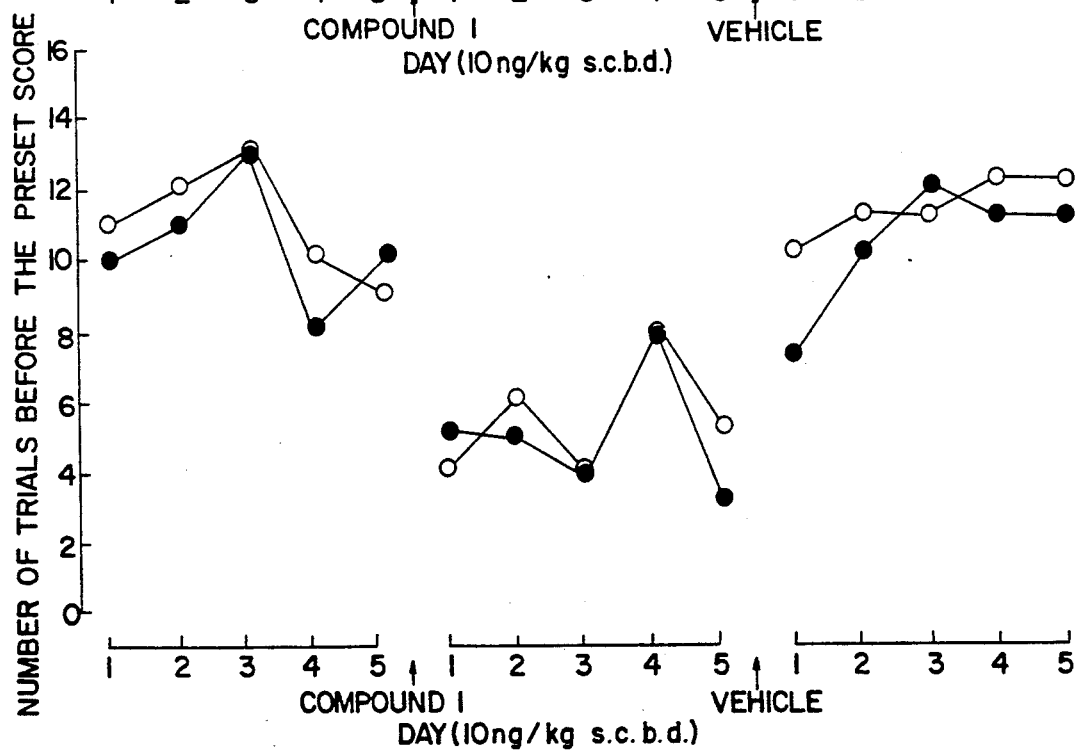

FIGS. 14A-14F represents the results of the measurements of one of the parameters used as an indication of the habituation process (the number of rearings in 5 minutes in the white compartment) in group of mice tested daily until habituation was established, as well as the effect on this parameter of the chronic administration of scopolamine, injected intraperitoneally at a dose of 0.25 mg/kg per day (FIG. 14A) and the effect on this parameter, after habituation and administration of scopolamine alone, of the administration of scopolamine, injected intraperitoneally at a dose of 0.25 mg/kg per day together with compound 1, injected subcutaneously at a dose of 1 ng/kg twice daily (FIG. 14B).

This study showed that administration of Compound 1 of the invention, after inhibition of the habituation by daily administration of scopolamine, enabled the behavior acquired before the scopolamine-induced disturbances to be re-established.

The compounds according to the invention improve the cognitive function in mice, and avert or inhibit deteriorations of that function caused, for example, by a disturbance of central cholinergic activity.

II - HABITUATION TEST IN OLD MICE

This test was carried out with an identical apparatus and under similar conditions to the Habituation Test In Young Mice as described above.

The same parameters (latency time, number of movements from place to place and rearings in each of the compartments and percentage of time spent in the dark compartment) were measured, and the effects of an injection of scopolamine were determined. The results were compared with those which were obtained with a group of young adult mice.

Since old mice are especially sensitive to the effects of scopolamine, scopolamine was injected at a dose of 0.1 mg/kg instead of 0.25 mg/kg for the group of young mice.

Finally, the effect of the Compound 1 of the invention (administered twice daily at a dose of 10 ng/kg) on the habituation and on the scopolamine-induced disturbances in old mice was determined by comparison with the results obtained with a control group of old mice.

RESULTS OF THE TEST

The results are shown in Tables 14 to 16.

From the results appearing in Table 14, it is apparent that old mice, in contrast to young mice, develop little in their faculty for perceiving the availability of a dark compartment. Although there is some degree of habituation, the results indicate that, even in a prolonged test situation, old mice manifest disorders of associative memory.

In as much as the learning potential of old mice is much inferior to that of young mice, the disturbances cause by scopolamine are relatively smaller (Table 15). However, these disturbances occur at a low dose which would have no effect on young mice.

From the results Table 16, it is apparent that treatment with the Compound 1 of the invention considerably improves learning in old mice, their performance parameters becoming equivalent to those of young mice, and averts the disturbances of habituation caused by scopolamine.

III - TEST OF ASSESSMENT OF COGNITIVE FUNCTION IN MARMOSETS

Marmoset monkeys were subjected to a test of acquisition of a capacity for selection and to a reverse learning test.

These tests are carried out using an apparatus known by the name of "Wisconsin General Test Apparatus" developed by Harlow in 1949 and described in Psychological Review 56, 51-65. This apparatus consists essentially of a cubic enclosure containing a board provided with wells into which a food bait can be introduced. These wells can be covered by various objects (stimuli).

The monkey is separated from the apparatus by an opaque shutter, which is opened by the investigator at the beginning of each trial. At that moment, the animal can touch a stimulus and receive the corresponding reward.

TEST PROCEDURE

Four 15- to 18-month male and female marmoset monkeys were used in this experiment.

One of the stimuli (positive stimulus) covered a well containing a reward, whereas the other (negative stimulus) covered an empty well.

Initially, the animals were trained to identify the positive stimulus, which was always the same but changed its position on the board.

The animals were tested for periods of 4 to 5 consecutive days, separated by rest periods of 2 days, until they obtained a result of 90 correct responses out of 100.

After interruption for one week, the trials were continued until a result of 18 correct responses out of 20, and the 9 correct responses out of 10, was obtained.

The protocol subsequently observed was of 5 days of tests, 2 days of rest, 5 days of tests, and so on.

The test compound was administered twice daily starting on the first day of the rest period. There were, accordingly, 5 days of tests without treatment, 2 days of treatment without a test and then 5 days of tests with treatment.

The tests were carried out with Compound 1 of the present invention, administered subcutaneously twice daily at a subanxiolytic dose of 10 ng/kg.

The test was continued until 6 consecutive correct trials were recorded, the result being represented by the number of trials carried out before these 6 correct responses were obtained.

In the reverse learning test, the positive stimulus of the above test became the negative stimulus, and vice versa. The result was also represented by the number of trials carried out before 6 consecutive correct responses were obtained.

RESULTS OF THE TEST

The results obtained with each of the monkeys, are illustrated in FIGS. 15A-15B and FIGS. 16A and 16B (by: •—• for acquisition of the capacity for selection; by o—o for reverse learning).

In the first test, the results obtained with each of the monkeys (monkeys nos. 1 to 4), 7-11, 4-12, 3-11 and 8-13 before treatment, changed to 2-6, 3-9, 0-8 and 3-8, respectively, after treatment with Compound 1 of the invention.

In the second test, the results, 11-14, 8-15, 6-14 and 9-13 before treatment, changed to 7-12, 8-12, 4-7 and 4-8 respectively, after treatment with Compound 1 of the invention.

It is apparent that Compound 1 of the invention improves learning, both in the case of a simple test such as that of acquisition of the capacity for selection, or a difficult test such as reverse learning.

The results demonstrate the activity of Compound 1 of the invention in the improvement of cognitive function. Similar results are obtained with other compounds of the invention.

In general, therapeutically acceptable results with the compounds of the invention can be preferably obtained at subcutaneous doses, twice a day, of from 1 mg/kg to 10 μg/kg. It will be recognized that greater or lesser amounts of the compounds can also be employed, depending on the particular result desired.

The results obtained in all the pharmacological tests described above show that the compounds of the invention can improve cognitive function as well as avert or remedy deterioration of the latter. They can, in particular, compensate disorders of cognitive function due to aging, which suggests that they may be efficacious in the treatment of Alzheimer's disease.

The invention is not to be limited except as set forth in the following claims:

TABLE 1

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
| --- | --- | --- | --- | --- | --- | --- | --- |
| | | Rearings in 5 minutes | Movements from place to place in 5 minutes | Rearings in 5 minutes | Movements from place to place in 5 minutes | | |
| Vehicle | 1 | 30 | 37 | 66 | 68 | 55 | 11 |
| Vehicle | 2 | 29 | 39 | 65 | 69 | 61 | 10.4 |
| Vehicle | 3 | 28 | 35 | 67 | 64 | 66 | 11.1 |
| Vehicle | 4 | 24 | 33 | 71 | 70 | 72 | 9.3 |
| Vehicle | 5 | 13 | 19 | 83 | 87 | 78 | 3.4 |
| Vehicle + scopolamine | 6 | 74+ | 87+ | 19+ | 20+ | 22+ | 20.2+ |

Vehicle: administered S.C. twice daily - Scopolamine: 0.25 mg/kg/I.P. n = 5 — S.E.M. < 10.4% — +p < 0.001 (impairment of learning by scopolamine).

TABLE 2

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
| --- | --- | --- | --- | --- | --- | --- | --- |
| | | Rearings in 5 minutes | Movements from place to place in 5 minutes | Rearings in 5 minutes | Movements from place to place in 5 minutes | | |
| Compound 1 | 1 | 31 | 34 | 67 | 67 | 56 | 10 |
| Compound 1 | 2 | 22 | 31 | 56 | 68 | 74* | 7.4 |
| Compound 1 | 3 | 9* | 11* | 90* | 90* | 76 | 2.6* |
| Compound 1 | 4 | 10* | 9* | 89* | 92* | 78 | immed.* |
| Compound 1 | 5 | 5 | 16 | 89 | 90 | 75 | 0.5 |
| Compound 1 + scopolamine | 6 | 11° | 12° | 86° | 90° | 75° | 0.7° |

Compound 1: 1 ng/kg/S.C. twice daily - Scopolamine: 0.25 mg/kg/I.P. n = 5 — S.E.M. < 13.5% — *P < 0.001 (learning significant compared with the control group). °P < 0.001 (antagonism of the impairment of learning by scopolamine).

TABLE 3

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
| --- | --- | --- | --- | --- | --- | --- | --- |
| | | Rearings in 5 minutes | Movements from place to place in 5 minutes | Rearings in 5 minutes | Movements from place to place in 5 minutes | | |
| Compound 2 | 1 | 26 | 41 | 58 | 70 | 57 | 12 |
| Compound 2 | 2 | 18 | 25* | 73* | 85* | 67* | 4 |
| Compound 2 | 3 | 8* | 11* | 99* | 97* | 73* | 3* |
| Compound 2 | 4 | 9* | 10* | 98* | 115* | 72* | 2* |
| Compound 2 | 5 | 10* | 16* | 87* | 89* | 69* | 2* |
| Compound 2 + scopolamine | 6 | 10*° | 13*° | 98*° | 102*° | 67*° | 2*° |

Compound 2: 10 ng/kg/S.C. twice daily - Scopolamine: 0.25 mg/kg/I.P. n = 5 — S.E.M. < 11.7% — *P < 0.001 (learning significant compared with D1). °P < 0.001 (antagonism of the impairment of learning by scopolamine).

TABLE 4

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
| --- | --- | --- | --- | --- | --- | --- | --- |
| | | Rearings in 5 minutes | Movements from place to place in 5 minutes | Rearings in 5 minutes | Movements from place to place in 5 minutes | | |
| Compound 3 | 1 | 24 | 31 | 53 | 67 | 52 | 10 |
| Compound 3 | 2 | 21 | 26 | 57 | 63 | 54 | 10 |
| Compound 3 | 3 | 13* | 19* | 79* | 80* | 65* | 3* |
| Compound 3 | 4 | 13* | 10* | 73* | 76* | 64* | 5* |
| Compound 3 | 5 | 14* | 21* | 72* | 77* | 65* | 4* |
| Compound 3 + | 6 | 12*° | 14*° | 89*° | 93*° | 70*° | 3*° |

TABLE 4-continued

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| scopolamine | | | | | | | |

Compound 3: 10 ng/kg/S.C. twice daily - Scopolamine: 0.25 mg/kg/I.P. n = 5 — S.E.M. < 12.7% — *P < 0.05 — P < 0.001 (learning significant compared with D1). °P < 0.001 (antagonism of the impairment of learning by scopolamine).

TABLE 5

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| Compound 4 | 1 | 28 | 36 | 71 | 80 | 51 | 12 |
| Compound 4 | 2 | 14* | 20* | 110* | 111* | 77* | 2* |
| Compound 4 | 3 | 10* | 15* | 101* | 104* | 67* | 2* |
| Compound 4 | 4 | 8* | 7* | 138* | 139* | 69* | 1* |
| Compound 4 | 5 | 9* | 8* | 103* | 117* | 73* | immediate* |
| Compound 4 + scopolamine | 6 | 10*° | 13*° | 121*° | 123*° | 79*° | 2*° |

Compound 4: 10 ng/kg/S.C. twice daily - Scopolamine: 0.25 mg/kg/I.P. n = 5 — S.E.M. < 11.7% — *P < 0.001 (learning significant compared with D1). °P < 0.001 (antagonism of the impairment of learning by scopolamine).

TABLE 6

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| Compound 5 | 1 | 23 | 33 | 69 | 71 | 59 | 11 |
| Compound 5 | 2 | 9* | 11* | 83* | 92* | 76* | 2* |
| Compound 5 | 3 | 6* | 11* | 89* | 96* | 82* | 3* |
| Compound 5 | 4 | 7* | 9* | 90* | 94* | 80* | 2* |
| Compound 5 | 5 | 5* | 8* | 92* | 103* | 79* | 2* |
| Compound 5 + scopolamine | 6 | 7° | 11° | 87° | 91° | 81° | 6° |

Compound 5: 1 μg/kg/S.C. twice daily - Scopolamine: 0.25 mg/kg/I.P. n = 5 — S.E.M. < 19% — *P < 0.05 — P < 0.001 (learning significant compared with D1). °P < 0.001 (antagonism of the impairment of learning by scopolamine).

TABLE 7

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| Compound 6 | 1 | 22 | 32 | 70 | 73 | 56 | 10 |
| Compound 6 | 2 | 11* | 9* | 86* | 101* | 80* | 3* |
| Compound 6 | 3 | 9* | 11* | 90* | 96* | 76* | 2* |
| Compound 6 | 4 | 6* | 9* | 81* | 103* | 78* | 2* |
| Compound 6 | 5 | 6* | 9* | 86* | 94* | 79* | 3* |
| Compound 6 + scopolamine | 6 | 7° | 9° | 92° | 100° | 82° | 4° |

Compound 6: 1 μg/kg/S.C. twice daily - Scopolamine: 0.25 mg/kg/I.P. n = 5 — S.E.M. < 21% — *P < 0.05 — P < 0.001 (learning significant compared with D1). °P < 0.001 (antagonism of the impairment of learning by scopolamine).

TABLE 8

HABITUATION OF YOUNG ADULT MICE
EFFECT OF ACUTE ADMINISTRATION OF SCOPOLAMINE

| TREATMENT | DAY | WHITE COMPARTMENT Rearings in 5 minutes | WHITE COMPARTMENT Movements from place to place in 5 minutes | BLACK COMPARTMENT Rearings in 5 minutes | BLACK COMPARTMENT Movements from place to place in 5 minutes | % TIME IN BLACK | LATENCY WHITE → BLACK (sec) |
|---|---|---|---|---|---|---|---|
| Compound 7 | 1 | 24 | 37 | 70 | 82 | 56 | 10 |
| Compound 7 | 2 | 11* | 12* | 96* | 111* | 76* | 2* |
| Compound 7 | 3 | 6* | 12* | 111* | 120* | 83* | 0* |
| Compound 7 | 4 | 9* | 8* | 121* | 106* | 74* | 2* |
| Compound 7 | 5 | 9* | 12* | 103* | 101* | 72* | 1.5* |
| Compound 7 + scopolamine | 6 | 5° | 11° | 112° | 120° | 70° | 3° |

Compound 7: 10 μg/kg/S.C. twice daily - Scopolamine: 0.25 mg/kg/I.P. n = 5 — S.E.M. < 20% — *P < 0.05 — P < 0.001 (learning significant compared with $D_1$). °P < 0.001 (antagonism of the impairment of learning by scopolamine).

TABLE 9

HABITUATION OF YOUNG ADULT MICE
EFFECT OF ACUTE ADMINISTRATION OF SCOPOLAMINE

| TREATMENT | DAY | WHITE COMPARTMENT Rearings in 5 minutes | WHITE COMPARTMENT Movements from place to place in 5 minutes | BLACK COMPARTMENT Rearings in 5 minutes | BLACK COMPARTMENT Movements from place to place in 5 minutes | % TIME IN BLACK | LATENCY WHITE → BLACK (sec) |
|---|---|---|---|---|---|---|---|
| Ref. A | 1 | 28 | 27 | 61 | 71 | 53 | 10 |
| Ref. A | 2 | 25 | 28 | 63 | 62 | 52 | 11 |
| Ref. A | 3 | 24 | 31 | 54 | 73 | 54 | 10 |
| Ref. A | 4 | 23 | 26 | 63 | 70 | 56 | 6 |
| Ref. A | 5 | 14* | 14* | 74* | 86* | 67* | 3* |
| Ref. A + scopolamine | 6 | 82+ | 88+ | 14+ | 19+ | 27+ | 17+ |

Reference compound A: 10 ng/kg/S.C. twice daily - Scopolamine: 0.25 mg/kg/I.P. n = 5 — S.E.M. < 12.6% — *P < 0.05 — P < 0.001 (learning significant compared with $D_1$). +P < 0.01 — P < 0.001 (impairment of learning by scopolamine).

TABLE 10

HABITUATION OF YOUNG ADULT MICE
EFFECT OF ACUTE ADMINISTRATION OF SCOPOLAMINE

| TREATMENT | DAY | WHITE COMPARTMENT Rearings in 5 minutes | WHITE COMPARTMENT Movements from place to place in 5 minutes | BLACK COMPARTMENT Rearings in 5 minutes | BLACK COMPARTMENT Movements from place to place in 5 minutes | % TIME IN BLACK | LATENCY WHITE → BLACK (sec) |
|---|---|---|---|---|---|---|---|
| Ref. A | 1 | 22 | 30 | 69 | 79 | 59 | 12 |
| Ref. A | 2 | 27 | 40 | 62 | 76 | 59 | 11 |
| Ref. A | 3 | 29 | 36 | 70 | 80 | 59 | 10 |
| Ref. A | 4 | 20 | 32 | 73 | 84 | 60 | 5 |
| Ref. A | 5 | 10* | 16* | 92* | 96* | 77* | 3* |
| Ref. A + scopolamine | 6 | 76+ | 80+ | 19+ | 23+ | 19+ | 22.5+ |

Reference compound A: 1 μg/kg/S.C. twice daily - Scopolamine: 0.25 mg/kg/I.P. n = 5 — S.E.M. < 26% — *P < 0.05 — P < 0.001 (learning significant compared with $D_1$). +P < 0.001 (impairment of learning by scopolamine).

TABLE 11

HABITUATION OF YOUNG ADULT MICE
EFFECT OF ACUTE ADMINISTRATION OF SCOPOLAMINE

| TREATMENT | DAY | WHITE COMPARTMENT Rearings in 5 minutes | WHITE COMPARTMENT Movements from place to place in 5 minutes | BLACK COMPARTMENT Rearings in 5 minutes | BLACK COMPARTMENT Movements from place to place in 5 minutes | % TIME IN BLACK | LATENCY WHITE → BLACK (sec) |
|---|---|---|---|---|---|---|---|
| Ref. B | 1 | 23 | 24 | 68 | 90 | 56 | 11 |
| Ref. B | 2 | 26 | 32 | 53 | 81 | 54 | 9 |
| Ref. B | 3 | 25 | 26 | 61 | 83 | 52 | 10 |
| Ref. B | 4 | 22 | 25 | 63 | 80 | 51 | 8 |
| Ref. B | 5 | 11* | 16* | 81* | 97 | 67* | 3* |
| Ref. B + | 6 | 19+ | 92+ | 18+ | 26+ | 21+ | 16+ |

TABLE 11-continued

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| scopolamine | | | | | | | |

Reference compound B: 10 ng/kg/S.C. twice daily - Scopolamine: 0.25 mg/kg/I.P. n = 5 — S.E.M. < 12.1% — *P < 0.05 — P < 0.001 (learning significant compared with D1). +P < 0.01 — P < 0.001 (impairment of learning by scopolamine).

TABLE 12

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| Ref. B | 1 | 27 | 36 | 71 | 83 | 57 | 12 |
| Ref. B | 2 | 29 | 42 | 76 | 80 | 63 | 13.5 |
| Ref. B | 3 | 26 | 33 | 80 | 80 | 62 | 11 |
| Ref. B | 4 | 13* | 12* | 86 | 86 | 72* | 7 |
| Ref. B | 5 | 11* | 12* | 94* | 97* | 79* | 3* |
| Ref. B + scopolamine | 6 | 63+ | 57+ | 30+ | 20+ | 20+ | 17.5+ |

Reference compound B: 1 μg/kg/S.C. twice daily - Scopolamine: 0.25 mg/kg/I.P. n = 5 — S.E.M. < 18.5% — *P < 0.05 — P < 0.001 (learning significant compared with D1). +P < 0.001 (impairment of learning by scopolamine).

TABLE 13

HABITUATION OF YOUNG ADULT MICE
EFFECT OF ACUTE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| Ref. C | 1 | 29 | 43 | 56 | 63 | 52 | 11 |
| Ref. C | 2 | 30 | 35 | 57 | 67 | 56 | 10 |
| Ref. C | 3 | 25 | 43 | 51 | 61 | 52 | 7 |
| Ref. C | 4 | 28 | 37 | 51 | 63 | 53 | 9 |
| Ref. C | 5 | 18* | 29* | 72* | 81* | 67* | 3* |
| Ref. C + scopolamine | 6 | 90+ | 86+ | 21+ | 26+ | 23+ | 20+ |

Reference compound C: 10 ng/kg/S.C. twice daily - Scopolamine: 0.25 mg/kg/I.P. n = 5 — S.E.M. < 12.9% — *P < 0.05 — P < 0.001 (learning significant compared with D1). +P < 0.001 (impairment of learning by scopolamine).

TABLE 14

HABITUATION PROCESS IN OLD MICE
COMPARISON WITH YOUNG ADULT MICE

| | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| OLD MICE | 1 | 38 | 48 | 43 | 48 | 41 | 12.5 |
| | 2 | 35 | 43 | 46 | 40 | 42 | 10.5 |
| | 3 | 40 | 47 | 40 | 39 | 52 | 10.5 |
| | 4 | 42 | 53 | 38 | 31 | 49 | 10 |
| | 5 | 36 | 39 | 47 | 57 | 56 | 8 |
| | 6 | 24 | 32 | 56 | 61 | 60 | 6 |
| | 7 | 22 | 32 | 55 | 58 | 61 | 6 |
| YOUNG MICE | 1 | 23 | 28 | 69 | 80 | 55 | 10 |
| | 2 | 22 | 24 | 72 | 83 | 57 | 11 |
| | 3 | 18 | 23 | 73 | 86 | 65 | 10 |
| | 4 | 9 | 12 | 90 | 96 | 72 | 6 |
| | 5 | 6 | 11 | 93 | 95 | 71 | 4 |
| | 6 | 7 | 12 | 87 | 92 | 75 | 3 |

TABLE 14-continued

HABITUATION PROCESS IN OLD MICE
COMPARISON WITH YOUNG ADULT MICE

| DAY | WHITE COMPARTMENT | | BLACK COMPARTMENT | | % TIME IN BLACK | LATENCY WHITE → BLACK (sec) |
|---|---|---|---|---|---|---|
| | Rearings in 5 minutes | Movements from place to place in 5 minutes | Rearings in 5 minutes | Movements from place to place in 5 minutes | | |
| 7 | 5 | 13 | 96 | 94 | 78 | 4 |

S.E.M. < 12.9%

TABLE 15

EFFECT OF SCOPOLAMINE ON THE HABITUATION PROCESS IN OLD MICE
COMPARISON WITH YOUNG ADULT MICE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| OLD | 1 | 40 | 44 | 45 | 52 | 39 | 10 |
| MICE | 2 | 33 | 49 | 40 | 47 | 40 | 9 |
| Scopolamine | 3 | 37 | 45 | 38 | 46 | 43 | 9 |
| (0.1 mg/kg)→ | 4 | 32 | 53 | 41 | 48 | 50 | 9 |
| | 5 | 30 | 39 | 48 | 58 | 52 | 7 |
| | 6 | 51+ | 67+ | 22+ | 27+ | 33+ | 18+ |
| | 7 | 31 | 40 | 43 | 55 | 51 | 8 |
| YOUNG | 1 | 20 | 25 | 62 | 75 | 51 | 10 |
| MICE | 2 | 22 | 25 | 69 | 75 | 53 | 11 |
| Scopolamine | 3 | 20 | 23 | 69 | 82 | 58 | 9 |
| (0.25 mg/kg)→ | 4 | 10 | 12 | 86 | 92 | 67 | 5 |
| | 5 | 6 | 9 | 91 | 94 | 73 | 4 |
| | 6 | 76+ | 78+ | 20+ | 12+ | 27+ | 26+ |
| | 7 | 7 | 6 | 83 | 82 | 75 | 3 | n = 5 − S.E.M. < 12.6% − +P < 0.05 − P < 0.001 (disturbances by scopolamine)

TABLE 16

HABITUATION OF OLD MICE
EFFECT OF THE ADMINISTRATION OF SCOPOLAMINE

| TREATMENT | DAY | WHITE COMPARTMENT | | BLACK COMPARTMENT | | % TIME IN BLACK | LATENCY WHITE → BLACK (sec) |
|---|---|---|---|---|---|---|---|
| | | Rearings in 5 minutes | Movements from place to place in 5 minutes | Rearings in 5 minutes | Movements from place to place in 5 minutes | | |
| Control Old | 1 | 39 | 42 | 43 | 50 | 40 | 40 |
| Mice | 2 | 37 | 45 | 43 | 44 | 42 | 9 |
| Scopolamine | 3 | 37 | 45 | 40 | 43 | 46 | 9 |
| (0.1 mg/kg) | 4 | 36 | 52 | 40 | 44 | 49 | 8\ |
| | 5 | 32 | 35 | 50 | 37 | 52 | 7 |
| | 6 | 57+ | 60+ | 18+ | 31+ | 37+ | 12+ |
| | 7 | 32 | 40 | 46 | 42 | 53 | 8 |
| Treated Old Mice | | | | | | | |
| Compound 1 | 1 | 30 | 29 | 53 | 78 | 53 | 8 |
| Compound 1 | 2 | 18* | 20* | 84* | 90* | 59* | 3* |
| Compound 1 | 3 | 18* | 21* | 80* | 86* | 62* | 2* |
| Compound 1 | 4 | 18* | 19* | 84* | 82* | 86* | 2* |
| Compound 1 | 5 | 18* | 20* | 81* | 80* | 87* | 1* |
| Compound 1 + Scopolamine (0.1 mg/kg) | 6 | 9° | 10° | 84° | 83° | 89° | 1° |
| Compound 1 | 7 | 10* | 11* | 84* | 83* | 84* | 1* | n = 5 − S.E.M. < 12.8% − *P < 0.001 (improved learning) - Compound 1: 10 ng/kg twice daily. +P < 0.05 − P < 0.001 (disturbances by scopolamine) - °P < 0.001 (antagonism of the effects of scopolamine).

What is claimed is:

1. A method of treating disorders of cognitive function which comprises administering to one in need of said treatment a daily dosage of 50 to 750 mg of a compound of the formula I:

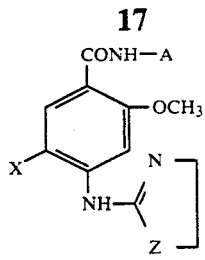

in which
A is diethylaminoethyl group or a group of the general formula II:

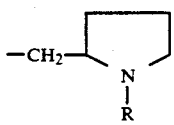

where R is a $C_1$-$C_3$ alkyl, allyl, cyclopropylmethyl or cyclohexenylmethyl group, X is a chlorine or bromine atom, and Z is —NH— or —O— with the following condition: when Z is —O—, A is a diethylaminoethyl group, and their pharmacologically acceptable salts.

2. The method of claim 1 employing the compound N-[2-(diethylamino)ethyl]-2-methoxy-4-[4,5-dihydro-1H-imidazol-2-yl)amino]-5-chlorobenzamide.

3. The method of claim 1 employing the compound N-(1-allyl-2-pyrrolidinylmethyl)-2-methoxy-4-[(4,5-dihydro-1H-imidazol-2-yl)amino]-5-chlorobenzamide.

4. The method of claim 1 employing the compound N-(1-methyl-2-pyrrolidinylmethyl)-2-methoxy-4-[4,5-dihydro-1H-imidazol-2-yl)amino]-5-chlorobenzamide.

5. The method of claim 1 employing the compound N-[2-(diethylamino)-ethyl]-2-methoxy-4-[4,5-dihydro-2-oxazolyl)amino]-5-chlorobenzamide.

6. The method of claim 1 employing the compound N-(1-cyclopropyl-methyl-2-pyrrolidinylmethyl)-2-methoxy-4-[4,5-dihydro-1H-imidazol-2-yl)amino]-5-chlorobenzamide.

7. The method of claim 1 employing the compound N-(1-cyclohexenyl-methyl-2-pyrrolidinylmethyl)-2-methoxy-4-[(4,5-dihydro-1H-imidazol-2-yl)amino]-5-chlorobenzamide.

8. The method of claim 1 employing the compound N-[2-(diethyl-amino)-ethyl]-2-methoxy 4-[4,5-dihydro-1H-imidazol-2-yl)amino]5-bromobenzamide.

9. The method of claim 1 employing the compound N-(1-propyl-2-pyrrolidinylmethyl)-2-methoxy-4-[4,5-dihydro-1H-imidazol-2-yl)amino]-5-chlorobenzamide.

* * * * *

UNITED STATES PATENT AND TRADEMARK OFFICE
CERTIFICATE OF CORRECTION

PATENT NO. : 5,110,824

DATED : May 5, 1992

INVENTOR(S) : Jacques Acher, et. al.

It is certified that error appears in the above-identified patent and that said Letters Patent is hereby corrected as shown below:

COLUMN 1

Line 16, "formed of" should read --formed the subject of--.

COLUMN 2

Line 16, "amino]5-" should read --amino]-5- --.

COLUMN 3

Line 22 should be deleted.
Line 23, "[4,5-dihydro-" should read --[(4,5-dihydro- --.
Line 26, "[4,5-dihydro-" should read --[(4,5-dihydro- --.
Line 31, "1 µm/kg." should read --1 µg/kg.--.
Line 36, "is" should read --are--.
Line 37, "represents" should read --represent--.
Line 45, "represents" should read --represent--.
Line 57, "FIGS. 4A-13F" should read --FIGS. 9A-13F--.

COLUMN 4

Line 47, "represents" should read --represent--.
Line 50, "group" should read --a group--.

COLUMN 5

Line 38, "results Table 16," should read --results appearing in Table 16,--.

UNITED STATES PATENT AND TRADEMARK OFFICE
CERTIFICATE OF CORRECTION

PATENT NO. : 5,110,824
DATED : May 5, 1992
INVENTOR(S) : JACQUES ACHER, ET AL.

It is certified that error appears in the above-identified patent and that said Letters Patent is hereby corrected as shown below:

COLUMN 6

Line 9, "the" should be deleted.

COLUMN 16

TABLE 16, " BLACK     should    -- BLACK
         (sec)      read         (sec)
          40  "                   10 --.

COLUMN 17

Line 27, "and" should read --or--.

COLUMN 18

Line 2, "[4,5-dihydro-" should read --[(4,5-dihydro- --.
Line 8, "[4,5-" should read --[(4,5- --.
Line 11, "[4,5-dihydro-" should read --[(4,5-dihydro- --.
Line 15, "[4,5-dihydro-" should read --[(4,5-dihydro- --.
Line 22, "2-methoxy 4-[4,5-dihydro-" should read
         --2-methoxy-4-[(4,5-dihydro- --.
Line 23, "amino]5" should read --amino]-5--.

UNITED STATES PATENT AND TRADEMARK OFFICE
CERTIFICATE OF CORRECTION

PATENT NO. : 5,110,824
DATED : May 5, 1992
INVENTOR(S) : JACQUES ACHER, ET AL.

It is certified that error appears in the above-identified patent and that said Letters Patent is hereby corrected as shown below:

COLUMN 18

Line 25, "[4,5-" should read --[(4,5- --.

Signed and Sealed this

Twenty-eighth Day of September, 1993

BRUCE LEHMAN

Attest:

Attesting Officer

Commissioner of Patents and Trademarks